US011065081B2

(12) United States Patent
Blair

(10) Patent No.: US 11,065,081 B2
(45) Date of Patent: Jul. 20, 2021

(54) STERILIZABLE WIRELESSLY DETECTABLE OBJECTS FOR USE IN MEDICAL PROCEDURES AND METHODS OF MAKING SAME

(71) Applicant: Covidien LP, Mansfield, MA (US)

(72) Inventor: William A. Blair, San Diego, CA (US)

(73) Assignee: COVIDIEN LP, Mansfield, MA (US)

(*) Notice: Subject to any disclaimer, the term of this patent is extended or adjusted under 35 U.S.C. 154(b) by 0 days.

(21) Appl. No.: 16/881,509

(22) Filed: May 22, 2020

(65) Prior Publication Data
US 2020/0281687 A1   Sep. 10, 2020

Related U.S. Application Data

(63) Continuation of application No. 15/540,324, filed as application No. PCT/US2016/014335 on Jan. 21, 2016, now Pat. No. 10,660,726.
(Continued)

(51) Int. Cl.
*A61B 90/98* (2016.01)
*G06K 19/07* (2006.01)
(Continued)

(52) U.S. Cl.
CPC .............. *A61B 90/98* (2016.02); *A61F 13/36* (2013.01); *A61F 13/44* (2013.01); *G06K 19/02* (2013.01);
(Continued)

(58) Field of Classification Search
CPC ..... A61B 90/98; G06K 19/02; G06K 19/0723; A61F 13/36; A61F 13/44
See application file for complete search history.

(56) References Cited

U.S. PATENT DOCUMENTS 2,740,405 A   4/1956   Riordan
3,031,864 A   5/1962   Freundlich
(Continued)

FOREIGN PATENT DOCUMENTS

AU   199852698 B2   3/1993
AU   2003249257 A1   2/2004
(Continued)

OTHER PUBLICATIONS

Bacheldor, "Surgical Sponges Get Smart" RFID Journal, Jul. 26, 2006, 2 pages.
(Continued)

*Primary Examiner* — Quan-Zhen Wang
*Assistant Examiner* — Mancil Littlejohn, Jr.

(57) ABSTRACT

Various embodiments of wirelessly detectable objects to be used in medical procedures are provided. Such may employ ionizing radiation hard wireless radio frequency identification (RFID) transponders, other wireless transponders and/or integrated circuits, and attachment structures, all of which retain structural and functional integrity when exposed to standard sterilization dosages of ionizing radiation. Additionally or alternatively, the wireless radio frequency identification (RFID) transponders, other wireless transponders and/or integrated circuits, and attachment structures, may retain structural and functional integrity when exposed to standard sterilization temperatures and/or pressures.

17 Claims, 12 Drawing Sheets

Related U.S. Application Data

(60) Provisional application No. 62/106,052, filed on Jan. 21, 2015, provisional application No. 62/138,248, filed on Mar. 25, 2015, provisional application No. 62/164,412, filed on May 20, 2015, provisional application No. 62/184,294, filed on Jun. 19, 2015.

(51) Int. Cl.
*G06K 19/02* (2006.01)
*A61F 13/36* (2006.01)
*A61F 13/44* (2006.01)
*A61B 90/00* (2016.01)
*A61F 13/15* (2006.01)

(52) U.S. Cl.
CPC .. *G06K 19/0723* (2013.01); *A61B 2090/0805* (2016.02); *A61B 2090/0813* (2016.02); *A61F 2013/15878* (2013.01)

(56) References Cited

U.S. PATENT DOCUMENTS

| | | |
|---|---|---|
| 3,123,210 A | 3/1964 | Hermanson et al. |
| 3,422,816 A | 1/1969 | Robinson et al. |
| 3,587,583 A | 6/1971 | Greenberg |
| 3,630,202 A | 12/1971 | Small |
| D240,166 S | 6/1976 | Vernon et al. |
| 4,034,297 A | 7/1977 | Giorgi et al. |
| 4,114,601 A | 9/1978 | Abels |
| 4,193,405 A | 3/1980 | Abels |
| D272,943 S | 3/1984 | Stone et al. |
| 4,477,256 A | 10/1984 | Hirsch |
| 4,540,398 A | 9/1985 | Barson et al. |
| 4,626,251 A | 12/1986 | Shen |
| 4,636,208 A | 1/1987 | Rath |
| 4,639,253 A | 1/1987 | Dyer et al. |
| 4,645,499 A | 2/1987 | Rupinskas |
| 4,658,818 A | 4/1987 | Miller, Jr. et al. |
| 4,681,111 A | 7/1987 | Silvian |
| 4,704,109 A | 11/1987 | Rupinskas |
| 4,718,897 A | 1/1988 | Elves |
| 4,893,118 A | 1/1990 | Lewiner et al. |
| 4,917,694 A | 4/1990 | Jessup |
| 4,935,019 A | 6/1990 | Papp, Jr. |
| 4,938,901 A | 7/1990 | Groitzsch et al. |
| 4,961,495 A | 10/1990 | Yoshida et al. |
| 4,992,675 A | 2/1991 | Conner, Jr. et al. |
| 5,041,103 A | 8/1991 | Rupinskas |
| 5,045,080 A | 9/1991 | Dyer et al. |
| 5,049,219 A | 9/1991 | Johns et al. |
| 5,057,095 A | 10/1991 | Fabian |
| 5,090,410 A | 2/1992 | Saper et al. |
| 5,105,829 A | 4/1992 | Fabian et al. |
| 5,107,862 A | 4/1992 | Fabian et al. |
| 5,112,325 A | 5/1992 | Zachry |
| D330,872 S | 11/1992 | Ball |
| 5,181,021 A | 1/1993 | Lee et al. |
| 5,188,126 A | 2/1993 | Fabian et al. |
| 5,190,059 A | 3/1993 | Fabian et al. |
| 5,203,767 A | 4/1993 | Cloyd |
| 5,224,593 A | 7/1993 | Bennett |
| 5,231,273 A | 7/1993 | Caswell et al. |
| 5,235,326 A | 8/1993 | Beigel et al. |
| 5,329,944 A | 7/1994 | Fabian et al. |
| 5,353,011 A | 10/1994 | Wheeler et al. |
| D353,343 S | 12/1994 | Eberhardt |
| D354,927 S | 1/1995 | Andrau |
| D356,052 S | 3/1995 | Andrau |
| D359,705 S | 6/1995 | Ball |
| 5,446,447 A | 8/1995 | Carney et al. |
| 5,456,718 A | 10/1995 | Szymaitis |
| 5,575,781 A | 11/1996 | DeBusk |
| D378,614 S | 3/1997 | Jensen |
| 5,650,596 A | 7/1997 | Morris et al. |
| 5,664,582 A | 9/1997 | Szymaitis |
| D385,037 S | 10/1997 | Jensen |
| 5,725,517 A | 3/1998 | DeBusk |
| 5,767,816 A | 6/1998 | Cosman |
| 5,792,128 A | 8/1998 | DeBusk |
| D412,135 S | 7/1999 | Saito |
| 5,923,001 A | 7/1999 | Morris et al. |
| 5,931,824 A | 8/1999 | Stewart et al. |
| 5,963,132 A | 10/1999 | Yoakum |
| 5,969,613 A | 10/1999 | Yeager et al. |
| D418,773 S | 1/2000 | Saito |
| 6,026,818 A | 2/2000 | Blair et al. |
| D423,673 S | 4/2000 | Bassoe |
| 6,093,869 A | 7/2000 | Roe et al. |
| D429,337 S | 8/2000 | Sanfilippo |
| 6,098,800 A | 8/2000 | Bennish, Jr. et al. |
| 6,171,985 B1 | 1/2001 | Joseph et al. |
| 6,172,608 B1 | 1/2001 | Cole |
| 6,201,469 B1 | 3/2001 | Balch et al. |
| 6,211,666 B1 | 4/2001 | Acker |
| 6,223,137 B1 | 4/2001 | McCay et al. |
| 6,232,878 B1 | 5/2001 | Rubin |
| 6,276,033 B1 | 8/2001 | Johnson et al. |
| 6,317,027 B1 | 11/2001 | Watkins |
| 6,349,234 B2 | 2/2002 | Pauly et al. |
| 6,353,406 B1 | 3/2002 | Lanzl et al. |
| 6,354,493 B1 | 3/2002 | Mon |
| 6,359,562 B2 | 3/2002 | Rubin |
| 6,366,206 B1 | 4/2002 | Ishikawa et al. |
| D456,907 S | 5/2002 | Sanfilippo |
| D457,634 S | 5/2002 | Rouns et al. |
| 6,384,296 B1 | 5/2002 | Roe et al. |
| 6,401,722 B1 | 6/2002 | Krag |
| 6,441,741 B1 | 8/2002 | Yoakum |
| D471,281 S | 3/2003 | Baura et al. |
| 6,557,752 B1 | 5/2003 | Yacoob |
| 6,566,997 B1 | 5/2003 | Bradin |
| 6,588,661 B2 | 7/2003 | Degrauwe et al. |
| 6,632,216 B2 | 10/2003 | Houzego et al. |
| 6,641,039 B2 | 11/2003 | Southard |
| 6,648,223 B2 | 11/2003 | Boukhny et al. |
| 6,650,143 B1 | 11/2003 | Peng |
| 6,650,240 B2 | 11/2003 | Lee et al. |
| 6,654,629 B2 | 11/2003 | Montegrande |
| 6,667,902 B2 | 12/2003 | Peng |
| 6,671,040 B2 | 12/2003 | Fong et al. |
| 6,696,954 B2 | 2/2004 | Chung |
| 6,700,151 B2 | 3/2004 | Peng |
| 6,734,795 B2 | 5/2004 | Price |
| 6,749,554 B1 | 6/2004 | Snow et al. |
| 6,753,783 B2 | 6/2004 | Friedman et al. |
| 6,766,960 B2 | 7/2004 | Peng |
| D495,055 S | 8/2004 | Silber |
| 6,774,800 B2 | 8/2004 | Friedman et al. |
| 6,777,623 B2 | 8/2004 | Ballard |
| 6,777,757 B2 | 8/2004 | Peng et al. |
| 6,778,089 B2 | 8/2004 | Yoakum |
| 6,786,405 B2 | 9/2004 | Wiedenhoefer |
| 6,791,891 B1 | 9/2004 | Peng et al. |
| 6,798,693 B2 | 9/2004 | Peng |
| 6,812,824 B1 | 11/2004 | Goldinger et al. |
| 6,812,842 B2 | 11/2004 | Dimmer |
| 6,822,570 B2 | 11/2004 | Dimmer et al. |
| 6,822,888 B2 | 11/2004 | Peng |
| 6,838,990 B2 | 1/2005 | Dimmer |
| 6,856,540 B2 | 2/2005 | Peng et al. |
| D502,419 S | 3/2005 | Copen |
| 6,861,639 B2 | 3/2005 | Al-Ali |
| 6,861,954 B2 | 3/2005 | Levin |
| 6,875,199 B2 | 4/2005 | Altman |
| 6,879,300 B2 | 4/2005 | Rochelle et al. |
| 6,898,116 B2 | 5/2005 | Peng |
| 6,909,366 B1 | 6/2005 | Marsh et al. |
| 6,940,751 B2 | 9/2005 | Peng et al. |
| D511,004 S | 10/2005 | Masuda |
| 6,951,305 B2 | 10/2005 | Overhultz et al. |
| 6,956,258 B2 | 10/2005 | Peng |
| D511,384 S | 11/2005 | Masuda |
| 6,972,986 B2 | 12/2005 | Peng et al. |
| 6,977,504 B2 | 12/2005 | Wright et al. |

(56) References Cited

U.S. PATENT DOCUMENTS

| | | |
|---|---|---|
| 6,992,925 B2 | 1/2006 | Peng |
| 6,998,541 B2 | 2/2006 | Morris et al. |
| 7,001,366 B2 | 2/2006 | Ballard |
| 7,019,650 B2 | 3/2006 | Volpi et al. |
| 7,026,924 B2 | 4/2006 | Degrauwe et al. |
| 7,026,927 B2 | 4/2006 | Wright et al. |
| 7,031,209 B2 | 4/2006 | Wang et al. |
| 7,037,336 B2 | 5/2006 | Ward |
| 7,042,722 B2 | 5/2006 | Suzuki et al. |
| D526,586 S | 8/2006 | McCaghren et al. |
| 7,098,793 B2 | 8/2006 | Chung |
| 7,118,029 B2 | 10/2006 | Nycz et al. |
| 7,135,973 B2 | 11/2006 | Kittel et al. |
| 7,135,978 B2 | 11/2006 | Gisselberg et al. |
| 7,142,118 B2 | 11/2006 | Hamilton et al. |
| 7,142,815 B2 | 11/2006 | Desjeux et al. |
| D534,448 S | 1/2007 | Shaffer, II et al. |
| 7,158,030 B2 | 1/2007 | Chung |
| 7,158,754 B2 | 1/2007 | Anderson |
| 7,159,832 B2 | 1/2007 | Easterling |
| 7,160,258 B2 | 1/2007 | Imran et al. |
| D536,673 S | 2/2007 | Silber |
| 7,176,419 B2 | 2/2007 | Ellis et al. |
| 7,176,798 B2 | 2/2007 | Dimmer et al. |
| 7,183,914 B2 | 2/2007 | Norman et al. |
| 7,183,927 B2 | 2/2007 | Kolton et al. |
| 7,196,289 B2 | 3/2007 | Ellis et al. |
| 7,227,469 B2 | 6/2007 | Varner et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,269,047 B1 | 9/2007 | Fong et al. |
| 7,299,981 B2 | 11/2007 | Hickle et al. |
| D557,423 S | 12/2007 | Chen |
| D558,352 S | 12/2007 | Sanfilippo |
| 7,307,530 B2 | 12/2007 | Fabian et al. |
| D558,882 S | 1/2008 | Brady |
| 7,319,396 B2 | 1/2008 | Homanfar et al. |
| 7,319,397 B2 | 1/2008 | Chung et al. |
| 7,325,723 B2 | 2/2008 | Desjeux |
| 7,333,013 B2 | 2/2008 | Berger |
| 7,342,497 B2 | 3/2008 | Chung et al. |
| 7,362,228 B2 | 4/2008 | Nycz et al. |
| D568,186 S | 5/2008 | Blair et al. |
| 7,382,255 B2 | 6/2008 | Chung |
| 7,397,364 B2 | 7/2008 | Govari |
| 7,399,899 B2 | 7/2008 | Fabian |
| 7,420,468 B2 | 9/2008 | Fabian et al. |
| 7,423,535 B2 | 9/2008 | Chung et al. |
| 7,446,646 B2 | 11/2008 | Huomo |
| 7,449,614 B2 | 11/2008 | Ales, III |
| 7,464,713 B2 | 12/2008 | Fabian et al. |
| 7,465,847 B2 | 12/2008 | Fabian |
| 7,471,541 B2 | 12/2008 | Fong et al. |
| D584,414 S | 1/2009 | Lash et al. |
| 7,474,222 B2 | 1/2009 | Yang et al. |
| 7,492,257 B2 | 2/2009 | Tethrake et al. |
| 7,492,261 B2 | 2/2009 | Cambre et al. |
| 7,492,263 B2 | 2/2009 | Marsilio et al. |
| 7,508,308 B2 | 3/2009 | Chung |
| D590,342 S | 4/2009 | Davila et al. |
| 7,513,425 B2 | 4/2009 | Chung |
| 7,541,933 B2 | 6/2009 | Volpi et al. |
| 7,557,710 B2 | 7/2009 | Sanchez et al. |
| D598,110 S | 8/2009 | Phillips et al. |
| D598,114 S | 8/2009 | Cryan |
| 7,596,850 B2 | 10/2009 | Barth et al. |
| 7,609,538 B1 | 10/2009 | Lee et al. |
| 7,644,016 B2 | 1/2010 | Nycz et al. |
| 7,696,877 B2 | 4/2010 | Barnes et al. |
| 7,703,674 B2 | 4/2010 | Stewart et al. |
| 7,769,422 B2 | 8/2010 | DiSilvestro et al. |
| 7,795,491 B2 | 9/2010 | Stewart et al. |
| 7,816,003 B1 | 10/2010 | Luchio |
| 7,837,694 B2 | 11/2010 | Tethrake et al. |
| 7,855,656 B2 | 12/2010 | Maschke |
| 7,876,097 B2 | 1/2011 | Greim |
| 7,898,420 B2 | 3/2011 | Blair et al. |
| 8,072,310 B1 | 12/2011 | Everhart |
| 8,082,192 B2 | 12/2011 | Nycz et al. |
| 8,105,296 B2 | 1/2012 | Morris et al. |
| 8,181,860 B2 | 5/2012 | Fleck et al. |
| 8,193,938 B2 | 6/2012 | Halberthal et al. |
| 8,256,674 B2 | 9/2012 | Fleck et al. |
| 8,259,518 B2 | 9/2012 | Peng et al. |
| 8,279,068 B2 | 10/2012 | Morris et al. |
| 8,358,212 B2 | 1/2013 | Blair |
| 8,454,613 B2 | 6/2013 | Tethrake et al. |
| 8,477,076 B1 | 7/2013 | Nero, Jr. et al. |
| 8,479,989 B2 | 7/2013 | Fleck et al. |
| 8,545,416 B1 | 10/2013 | Kayyali et al. |
| 8,576,076 B2 | 11/2013 | Morris et al. |
| 8,624,721 B2 | 1/2014 | Barker, Jr. et al. |
| 8,710,957 B2 | 4/2014 | Blair et al. |
| 8,726,911 B2 * | 5/2014 | Blair ............... A61F 13/00051 128/899 |
| 8,780,660 B2 | 7/2014 | Peng |
| 8,797,820 B2 | 8/2014 | Peng et al. |
| 8,872,662 B2 | 10/2014 | Halberthal et al. |
| 8,878,668 B2 | 11/2014 | Blair et al. |
| 8,978,229 B2 | 3/2015 | Halberthal et al. |
| 8,985,446 B2 | 3/2015 | Fleck et al. |
| 8,994,358 B2 | 3/2015 | McElhinny et al. |
| 9,041,479 B2 | 5/2015 | Nero, Jr. et al. |
| 9,089,366 B2 | 7/2015 | Garner-Richards et al. |
| 9,119,667 B2 | 9/2015 | Halberthal et al. |
| 9,168,104 B2 | 10/2015 | Dein |
| 9,414,973 B2 | 8/2016 | Fleck et al. |
| 9,507,981 B2 | 11/2016 | Dor et al. |
| 9,530,036 B2 | 12/2016 | Fleck et al. |
| 9,672,397 B2 | 6/2017 | Fleck et al. |
| 9,717,565 B2 | 8/2017 | Blair |
| 9,730,850 B2 | 8/2017 | Blair et al. |
| 9,763,742 B2 | 9/2017 | Blair |
| 9,792,408 B2 | 10/2017 | Blair et al. |
| 9,814,540 B2 | 11/2017 | Blair et al. |
| 10,660,726 B2 | 5/2020 | Blair |
| 2001/0000659 A1 | 5/2001 | Hayashi et al. |
| 2001/0030610 A1 | 10/2001 | Rochelle et al. |
| 2002/0011932 A1 | 1/2002 | Rodgers et al. |
| 2002/0032435 A1 | 3/2002 | Levin |
| 2002/0070863 A1 | 6/2002 | Brooking |
| 2002/0143320 A1 | 10/2002 | Levin |
| 2002/0188259 A1 | 12/2002 | Hickle et al. |
| 2003/0004411 A1 | 1/2003 | Govari et al. |
| 2003/0052788 A1 | 3/2003 | Chung |
| 2003/0105394 A1 | 6/2003 | Fabian et al. |
| 2003/0111592 A1 | 6/2003 | Al-Ali |
| 2004/0008123 A1 | 1/2004 | Carrender et al. |
| 2004/0129279 A1 | 7/2004 | Fabian et al. |
| 2004/0137844 A1 | 7/2004 | Desjeux et al. |
| 2004/0138554 A1 | 7/2004 | Dimmer et al. |
| 2004/0250819 A1 | 12/2004 | Blair et al. |
| 2005/0049564 A1 | 3/2005 | Fabian |
| 2005/0110640 A1 | 5/2005 | Chung |
| 2005/0131397 A1 | 6/2005 | Levin |
| 2005/0154293 A1 | 7/2005 | Gisselberg et al. |
| 2005/0203470 A1 | 9/2005 | Ballard |
| 2005/0212673 A1 | 9/2005 | Forster |
| 2005/0247794 A1 | 11/2005 | Jones et al. |
| 2005/0249036 A1 | 11/2005 | Davies et al. |
| 2005/0267550 A1 | 12/2005 | Hess et al. |
| 2006/0054107 A1 | 3/2006 | Baker |
| 2006/0084934 A1 | 4/2006 | Frank |
| 2006/0106368 A1 | 5/2006 | Miller et al. |
| 2006/0187044 A1 | 8/2006 | Fabian et al. |
| 2006/0194899 A1 | 8/2006 | Ohashi et al. |
| 2006/0202827 A1 | 9/2006 | Volpi et al. |
| 2006/0232407 A1 | 10/2006 | Ballard |
| 2006/0235488 A1 | 10/2006 | Nycz et al. |
| 2006/0241396 A1 | 10/2006 | Fabian et al. |
| 2006/0241399 A1 * | 10/2006 | Fabian ............... A61B 5/061 600/424 |
| 2006/0244597 A1 | 11/2006 | Tethrake et al. |

(56) References Cited

U.S. PATENT DOCUMENTS

| | | |
|---|---|---|
| 2006/0270933 A1 | 11/2006 | Benson et al. |
| 2007/0000605 A1 | 1/2007 | Millette et al. |
| 2007/0004994 A1 | 1/2007 | Sherman |
| 2007/0005141 A1 | 1/2007 | Sherman |
| 2007/0034670 A1 | 2/2007 | Racenet et al. |
| 2007/0038233 A1 | 2/2007 | Martinez et al. |
| 2007/0051473 A1 | 3/2007 | Speich |
| 2007/0055109 A1 | 3/2007 | Bass et al. |
| 2007/0069866 A1 | 3/2007 | Schuessler et al. |
| 2007/0075176 A1 | 4/2007 | Andrews et al. |
| 2007/0109099 A1 | 5/2007 | Raphaeli et al. |
| 2007/0112649 A1 | 5/2007 | Schlabach |
| 2007/0125392 A1 | 6/2007 | Olson, Jr. et al. |
| 2007/0152823 A1 | 7/2007 | Hirahara et al. |
| 2007/0160494 A1 | 7/2007 | Sands |
| 2007/0209957 A1 | 9/2007 | Glenn et al. |
| 2007/0216062 A1 | 9/2007 | Frank |
| 2007/0216526 A1 | 9/2007 | Volpi et al. |
| 2007/0219516 A1 | 9/2007 | Patel et al. |
| 2007/0238982 A1 | 10/2007 | Caylor, III |
| 2007/0239289 A1 | 10/2007 | Cambre et al. |
| 2007/0265690 A1 | 11/2007 | Lichtenstein et al. |
| 2007/0270660 A1 | 11/2007 | Caylor, III et al. |
| 2007/0281153 A1 | 12/2007 | Yamamoto |
| 2008/0001760 A1 | 1/2008 | Oh et al. |
| 2008/0007411 A1 | 1/2008 | Levin |
| 2008/0018432 A1 | 1/2008 | Volpi et al. |
| 2008/0020189 A1 | 1/2008 | Hofmair et al. |
| 2008/0021308 A1 | 1/2008 | Dimmer et al. |
| 2008/0024277 A1 | 1/2008 | Volpi et al. |
| 2008/0030303 A1 | 2/2008 | Kobren et al. |
| 2008/0048855 A1 | 2/2008 | Berger |
| 2008/0051746 A1 | 2/2008 | Shen-Gunther |
| 2008/0086771 A1 | 4/2008 | Li et al. |
| 2008/0126122 A1 | 5/2008 | Warner et al. |
| 2008/0132860 A1 | 6/2008 | Smith et al. |
| 2008/0231452 A1 | 9/2008 | Levin |
| 2008/0275327 A1 | 11/2008 | Faarbaek et al. |
| 2008/0281190 A1 | 11/2008 | Petcavich et al. |
| 2008/0296373 A1* | 12/2008 | Zmood .............. G06K 19/0672 235/385 |
| 2009/0008449 A1 | 1/2009 | Qing et al. |
| 2009/0051485 A1 | 2/2009 | Corry et al. |
| 2009/0267765 A1 | 10/2009 | Greene et al. |
| 2009/0315681 A1 | 12/2009 | Blair |
| 2009/0322485 A1 | 12/2009 | Barnes et al. |
| 2010/0033309 A1 | 2/2010 | Blair |
| 2010/0057167 A1 | 3/2010 | Evers et al. |
| 2010/0108079 A1 | 5/2010 | Blair |
| 2010/0109848 A1 | 5/2010 | Blair et al. |
| 2010/0179822 A1 | 7/2010 | Reppas |
| 2010/0259393 A1 | 10/2010 | Marur et al. |
| 2011/0181394 A1 | 7/2011 | Blair |
| 2012/0031547 A1 | 2/2012 | Halberthal et al. |
| 2012/0116499 A1 | 5/2012 | Goetzen et al. |
| 2013/0088354 A1 | 4/2013 | Thomas |
| 2013/0105585 A1 | 5/2013 | Chakravarty |
| 2013/0199720 A1 | 8/2013 | Halberthal et al. |
| 2014/0243770 A1 | 8/2014 | Stewart |
| 2015/0216610 A1 | 8/2015 | Augustine |
| 2015/0272688 A1 | 10/2015 | Blair et al. |
| 2015/0317555 A1 | 11/2015 | Dor et al. |
| 2015/0320506 A1 | 11/2015 | Sayles |
| 2015/0375041 A1* | 12/2015 | Richley .................. H04L 43/04 340/870.07 |
| 2016/0070942 A1 | 3/2016 | Dor et al. |
| 2016/0135895 A1 | 5/2016 | Faasse et al. |
| 2016/0157957 A1 | 6/2016 | Blair |
| 2016/0210548 A1 | 7/2016 | Blair |
| 2016/0212577 A1 | 7/2016 | Dor et al. |
| 2016/0250000 A1 | 9/2016 | Blair |
| 2017/0027660 A1 | 2/2017 | Blair |
| 2017/0296301 A1 | 10/2017 | Dor et al. |
| 2017/0348172 A1 | 12/2017 | Blair et al. |
| 2018/0000555 A1 | 1/2018 | Blair |

FOREIGN PATENT DOCUMENTS

| | | |
|---|---|---|
| CA | 1171260 A | 7/1984 |
| CN | 101460096 A | 6/2009 |
| CN | 101896131 A | 11/2010 |
| EP | 1612554 A1 | 1/2006 |
| EP | 2087850 A2 | 8/2009 |
| JP | 2009539478 A | 11/2009 |
| WO | 8602539 A1 | 5/1986 |
| WO | 0239917 A1 | 5/2002 |
| WO | 03073934 A1 | 9/2003 |
| WO | 2004008387 A1 | 1/2004 |
| WO | 2004054801 A1 | 7/2004 |
| WO | 2004086997 A1 | 10/2004 |
| WO | 2006060781 A1 | 6/2006 |
| WO | 2007120736 A2 | 10/2007 |
| WO | 2008008449 A2 | 1/2008 |
| WO | 2008024921 A2 | 2/2008 |
| WO | 2007146091 A3 | 7/2008 |
| WO | 2008106552 A1 | 9/2008 |
| WO | 2008112709 A1 | 9/2008 |
| WO | 2008133634 A1 | 11/2008 |
| WO | 2009151946 A2 | 12/2009 |
| WO | 2009154987 A2 | 12/2009 |
| WO | 2010134826 A1 | 11/2010 |

OTHER PUBLICATIONS

Barnes et al., "Method, Apparatus and Article for Detection of Transponder Tagged Objects, for Example During Surgery," U.S. Appl. No. 61/056,787, filed May 28, 2008, 60 pages.

Barnes et al., "Method, Apparatus and Article for Detection of Transponder Tagged Objects, for Example During Surgery," U.S. Appl. No. 61/091,667, filed Aug. 25, 2008, 76 pages.

Blair et al., "Apparatus and Method for Detecting Objects Using Tags and Wideband Detection Device," U.S. Appl. No. 60/811,376, filed Jun. 6, 2006.

Blair et al., "Mat Based Antenna System to Detect Transponder Tagged Objects, for Example During Medical Procedures," U.S. Appl. No. 61/453,846, filed Mar. 17, 2011, 38 pages.

Blair et al., "Method and Apparatus to Detect Transponder Tagged Objects and to Communicate With Medical Telemetry Devices, for Example During Medical Procedures," U.S. Appl. No. 15/786,001, filed Oct. 17, 2017, 160 pages.

Blair et al., "Method and Apparatus to Detect Transponder Tagged Objects and to Communicate with Medical Telemetry Devices, for Example During Medical Procedures," U.S. Appl. No. 61/242,699, filed Sep. 15, 2009, 158 pages.

Blair et al., "Method and Apparatus to Detect Transponder Tagged Objects and to Communicate with Medical Telemetry Devices, for Example During Surgery," U.S. Appl. No. 61/222,847, filed Jul. 2, 2009, 122 pages.

Blair et al., "Method and Apparatus to Detect Transponder Tagged Objects, for Example During Medical Procedures," U.S. Appl. No. 61/242,704, filed Sep. 15, 2009, 127 pages.

Blair et al., "Method and Apparatus to Detect Transponder Tagged Objects, for Example During Surgery," U.S. Appl. No. 61/109,104, filed Oct. 28, 2008, 73 pages.

Blair et al., "Method and Apparatus to Detect Transponder Tagged Objects, for Example During Surgery," U.S. Appl. No. 61/222,443, filed Jul. 1, 2009, 95 pages.

Blair et al., "Method, Apparatus and Article for Detection of Transponder Tagged Objects, for Example During Surgery," U.S. Appl. No. 60/892,208, filed Feb. 28, 2007, 50 pages.

Blair et al., "Tag and Detection Device," U.S. Appl. No. 60/458,222, filed Mar. 27, 2003, 23 pages.

Blair et al., "Transponder Housing and Device to Mark Implements, Such as Surgical Implements, and Method of Using Same," U.S. Appl. No. 60/894,435, filed Mar. 12, 2007, 30 pages.

Blair, "Apparatus, Method, and Article for Detection and Identification of Multi-Mode Integral Transponder Tagged Objects," U.S. Appl. No. 61/056,229, filed May 27, 2008, 38 pages.

(56) References Cited

OTHER PUBLICATIONS

Blair, "Apparatuses to Physically Couple Transponder to Objects, Such as Surgical Objects, and Methods of Using Same," U.S. Appl. No. 62/121,358, filed Feb. 26, 2015, 88 pages.
Blair, "Article to Attach a Transponder to a Surgical Sponge," U.S. Appl. No. 29/336,009, filed Apr. 27, 2009, 4 pages.
Blair, "Attachment Article to Attach a Transponder to a Surgical Sponge," U.S. Appl. No. 29/336,007, filed Apr. 27, 2009, 4 pages.
Blair, "Attachment Article to Attach a Transponder to a Surgical Sponge," U.S. Appl. No. 29/336,008, filed Apr. 27, 2009, 7 pages.
Blair, "Detectable Surgical Objects and Methods of Making Same," U.S. Appl. No. 61/109,142, filed Oct. 28, 2008, 47 pages.
Blair, "Method and Apparatus to Account for Transponder Tagged Objects Used During Medical Procedures," U.S. Appl. No. 61/263,726, filed Nov. 23, 2009, 78 pages.
Blair, "Multi-Modal Transponder and Method and Apparatus to Detect Same," U.S. Appl. No. 61/102,749, filed Oct. 3, 2008, 48 pages.
Blair, "Radio Opaque Device With Resonant Nanostructures," U.S. Appl. No. 61/163,813, filed Mar. 26, 2009, 47 pages.
Blair, "Transponder Device to Mark Implements, Such as Surgical Implements, and Method of Manufacturing and Using Same," U.S. Appl. No. 61/086,727, filed Aug. 6, 2008, 30 pages.
Blair, "Transponder Device to Mark Implements, Such as Surgical Implements, and Method of Manufacturing and Using Same," U.S. Appl. No. 61/220,452, filed Jun. 25, 2009, 46 pages.
Blair, "Transponder Device to Mark Implements, Such as Surgical Implements, and Method of Manufacturing and Using Same," U.S. Appl. No. 61/224,323, filed Jul. 9, 2009, 57 pages.
Blair, "Transponder Housing," U.S. Appl. No. 29/322,539, filed Aug. 6, 2008, 6 pages.
Clearcount Medical Solutions, "The SmartSponge System," Downloaded Oct. 20, 2009.
Extended European Search Report, dated Jul. 30, 2015, for European Application No. 14176398.7, 7 pages.
Haldor Advanced Technologies, "Haldor Advanced Technologies Releases a Breakthrough New Sponge Management Solution: Modular, Mobile, Wireless, and Tailored per Use—case and Requirements," Sep. 8, 2015, retrieved fromhttp://ww1.prweb.com/prfiles/2015/09/06/12938762/ORLocate%205Sponge%20Sol-ution-September%202015.pdf, 2 pages.
International Search Report and Written Opinion, dated May 2, 2016, for International Application No. PCT/US2016/014324, 18 pages.
International Search Report, dated Dec. 23, 2014, for PCT/US2014/045942, 3 pages.
Macario, et al., "Initial Clinical Evaluation of a Handheld Device for Detecting Retained Surgical Gauze Sponges Using Radiofrequency Identification Technology," Arch. Surg., vol. 14, Jul. 2005, pp. 659-662.
Merritt et al., "Detectable Sponges for Use in Medical Procedures and Methods of Making, Packaging, and Accounting for Same," U.S. Appl. No. 15/540,331, filed Jun. 28, 2017, 54 pages.
Technologies Solutions Group, "ORtrack," 2013, 2 pages.
Technologies Solutions Group, "Sponge-Track," 2013, 2 pages.
Written Opinion, dated Dec. 23, 2014, for PCT/US2014/045942, 7 pages.
International Search Report for (PCT/US2016/014335) dated May 12, 2016 (3 pages).
Extended European Search Report, dated Jun. 12, 2018, for European Application No. 16740758.4-1113, 11 pages.
Australian Examination Report No. 1 dated Aug. 7, 2019 corresponding to counterpart Patent Application AU 2016200113.
Chinese First Office Action dated Jul. 3, 2019 corresponding to counterpart Patent Application CN 201610035445.2.
Chinese Search Report dated Jun. 25, 2019 corresponding to counterpart Patent Application CN 201610035445.2.

* cited by examiner

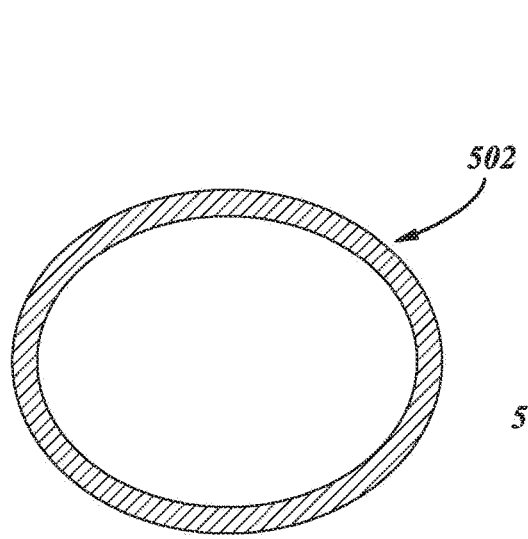
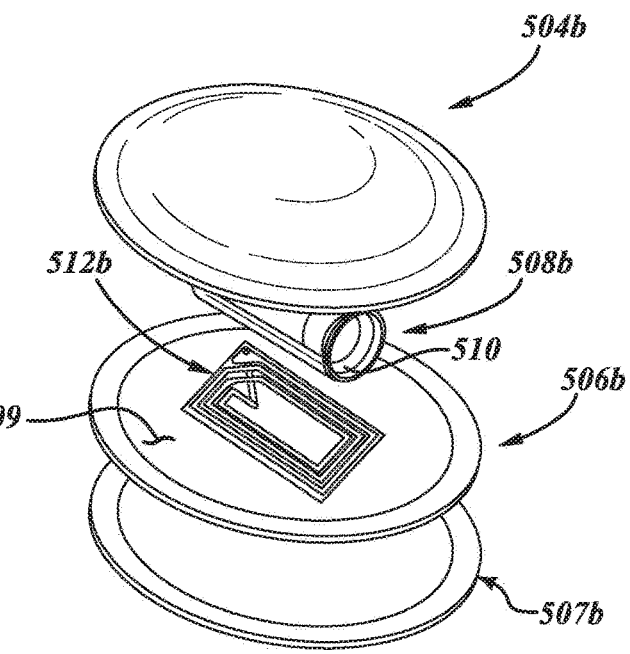
FIG.5A
FIG.5B
FIG.5C
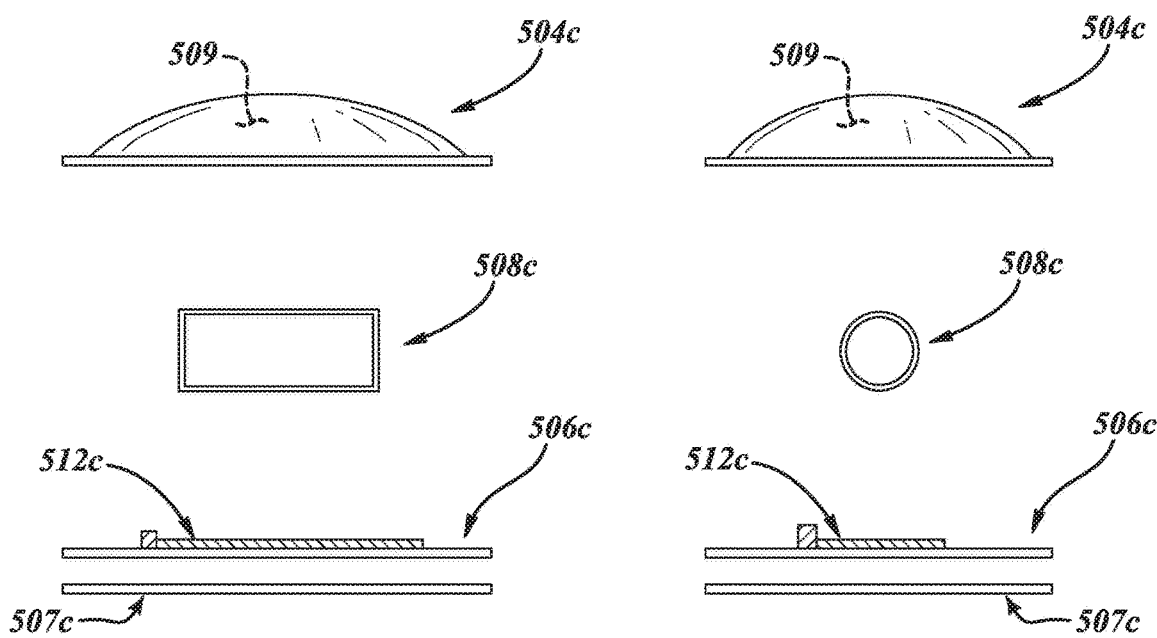

STERILIZABLE WIRELESSLY DETECTABLE OBJECTS FOR USE IN MEDICAL PROCEDURES AND METHODS OF MAKING SAME

CROSS-REFERENCE TO RELATED APPLICATIONS

This application is a Continuation Application of U.S. patent application Ser. No. 15/540,324, filed Jun. 28, 2017, now published as U.S. Patent Publication No. 2018/0000556, which is a U.S. national stage application filed under 35 U.S.C. § 371 of International Patent Application PCT/US2016/014335, accorded an international filing date of Jan. 21, 2016, which claims the benefit of U.S. Provisional Patent Ser. Nos. 62/106,052 filed Jan. 21, 2015; 62/138,248 filed Mar. 25, 2015; 62/164,412 filed May 20, 2015; and 62/182,294 filed Jun. 19, 2015, which applications are incorporated herein by reference in their entirety.

BACKGROUND

Technical Field

The present disclosure generally relates to medical procedure related objects (e.g., sponges, instruments, tools, etc.) tagged with wirelessly readable wireless transponders.

Description of Related Art

It is important to determine ascertain that objects associated with surgery or other medical procedures (e.g., labor and delivery (L&D)) are not present in a patient's body before completion of surgery or other medical procedure to prevent unintended retention of what are considered foreign objects with respect to the body. Such medical procedure objects may take a variety of forms. For example, the medical procedure objects may take the form of instruments or tools, for instance scalpels, scissors, forceps, hemostats, endoscopes, clips and/or clamps. Also for example, the medical procedure objects may take the form of disposable or consumable objects, for instance surgical sponges, gauzes, and/or pads. Failure to locate a medical procedure object before completing the medical procedure (e.g., closing the incision or wound of the patient) may require additional medical procedures to retrieve the medical procedure object (e.g., additional surgeries) exposing the patient to further trauma, complications and inconvenience. In some instances, failure to locate a medical procedure object may have serious adverse medical consequences, for example due to an infection leading to sepsis and possible death. Additionally, failure to locate a medical procedure object may also result in significant additional costs in providing medical care.

Most hospitals and other clinical facilities have instituted procedures that employ checklists and/or require multiple manual counts to be performed to determine the total number of medical procedure objects at a start of and at an end of a medical procedure. These processes may be denominated as manual count-in/count-out or check-in/check-out processes, since they typically employ a manual counting at a start and an end of a medical procedure or checking in and checking out of the medical procedure objects. These manual approaches are inefficient, requiring the time of highly trained personnel, and are prone to error.

Another approach marks various objects with optically readable machine-readable symbols, which each encode a respective unique identifiers. These machine-readable symbols may take various forms, for instance linear or one-dimensional machine-readable symbols, commonly referred to as barcode symbols, or two-dimensional symbols, typically denominated as area or matrix code symbols. The symbols may be encoded according to any of a large variety of symbologies (e.g., mappings between machine-readable characters and human-readable characters). The optically readable symbols may be printed on respective tags or labels, which are attached to the respective medical procedure objects, for instance via an adhesive. Symbols may alternatively be etched or otherwise inscribed on respective medical procedure objects. In use, a machine-readable symbol reader (e.g., barcode scanner) may illuminate the machine-readable symbol and automatically read a unique identifier encoded therein. The process tends to mimic the manual count-in/count-out or check-in/check-out processes, that is each item is scanned prior to or at the start of a medical procedure, and then scanned again following or at the end of the medical procedure. A processor-based device may perform an automated comparison, providing an alert when the list of medical procedure objects at the end of the medical procedure does not match the list of medical procedure objects at the start of the medical procedure.

Yet another approach marks various objects with wirelessly readable transponders, each transponder encoding a respective unique identifier. These wirelessly readable transponders are commonly referred to as radio frequency identification (RFID) tags or transponders, even though the RFID transponders may operate in the high radio frequency or even microwave portions of the electromagnetic spectrum. These RFID transponders typically include a memory in the form of an integrated circuit, for example a read/writable memory which can be read many times and written too many times. Typically, RFID transponders are passive devices, without a battery. These passive RFID transponders derive electrical energy from an interrogation signal transmitted by an RFID reader or interrogator. The RFID transponders may be attached to respective ones of the medical procedure objects. In use, an RFID reader or interrogator emits a radio or microwave frequency signal. In response, an RFID transponder that receives the interrogation signal charges a capacitor, which provides sufficient power to return (e.g., backscatter) a response signal that encodes the unique identifier stored in the RFID transponder. The interrogator receives the return signal identifying the respective RFID transponder. The process tends to mimic the manual count-in/count-out or check-in/check-out processes, that is each item is scanned prior to or at the start of a medical procedure, and then scanned again following or at the end of the medical procedure. A processor-based device may perform an automated comparison, providing an alert when the list of medical procedure objects at the end of the medical procedure does not match the list of medical procedure objects at the start of the medical procedure.

Another approach employs wirelessly detectable transponders and a wireless detection system. This approach typically employs simple LC resonant wireless transponders, which do not encode or return any unique identifying information, thus may be denominated as or "dumb" wireless transponders. These dumb wireless transponders that are attached to various medical procedure objects using a variety of structures (e.g., adhesives, epoxy, potting material, housings). The wireless detection system includes one or more radios, with a transmitter that emits pulsed wideband wireless excitation signals (e.g., radio or microwave frequency) and a receiver or detector that detects wireless return or response signals returned by the dumb wireless transponders in response to the emitted pulsed wideband signals. In use, the wireless detection system scans a body or portion of a body of a patient for the presence or absence of a dumb wireless transponder. Such an automated detection system may operate at relatively low frequencies ranges, advantageously increasing accuracy particularly where the dumb transponder may be located in vivo (i.e., in bodily tissue) as compared to RFID based approaches. Such an automated detection system may also significantly reduce the amount of time required of highly trained and highly compensated personnel as compared to the previously described approaches. Some examples of the dumb transponder and wireless detector approach are discussed in U.S. Pat. No. 6,026,818, issued Feb. 22, 2000, and U.S. Patent Publication No. U.S. 2004/0250819, published Dec. 16, 2004. The dumb transponder and wireless detector approach contrasts to previously described approaches, since this approach does rely on the previously described count-in/count-out or check-in/check-out techniques common of the previously described approaches.

The medical procedure object must be sterilized prior to use in a medical procedure. Sterilization procedures typically take one or more forms, including heating, pressurization, and/or exposure to ionizing radiation (e.g., Gamma radiation).

BRIEF SUMMARY

In any of the above-described approaches, anything attached to the medical procedure object (e.g., machine-readable symbol, RFID wireless transponder, dumb wireless transponder) must like-wise be capable of undergoing sterilization procedures. However, sterilization procedures may have a damaging effect on integrated circuits, semiconductor-based devices and/or associated attachment structures (e.g., adhesives). For example, many integrated circuits or semiconductor-based devices (e.g., memory) are adversely affected by exposure to Gamma radiation that may render data or information unreliable. Also, various adhesives or polymers (e.g., plastics) are adversely affected by heat, pressure, a combination of heat and pressure, and/or ionizing radiation (e.g., X-ray, Gamma ray radiation).

Consequently, new approaches, structures and techniques are desirable to facilitate the marking of medical device objects and automated detection of the same in bodily tissue and/or inventorying of the same for use in performing medical procedures, and prevention of unintentional retention of a foreign object retention in a body cavity or tissue.

The use of materials that can withstand sterilization may be advantageous where a medical procedure object will undergo sterilization prior to use, or may be subject to repeated sterilization procedures, for instance in preparation for reuse or repeated use for multiple different medical procedures.

A radiation hard (e.g., X-ray, Gamma ray radiation hard) RFID transponder, other wireless transponder and/or integrated circuit, particularly a radiation hard read-only (i.e., write once) memory, which encodes a unique identifier, may be particularly useful in marking and identifying medical procedure objects to be used during a medical procedure. Such may be used to mark durable or reusable or medical procedure objects, for instance medical instruments or tools, as well as to mark disposable or consumable medical procedure objects, for instance gauzes or sponges. Additionally or alternatively, the RFID transponder, other wireless transponder and/or integrated circuit may also be composed of materials that withstand elevated heat or temperatures, elevated pressures, and/or combinations of elevated heat or temperatures and pressures commonly experienced during sterilization procedures.

Optionally, a radiation hard integrated circuit may take the form of a radiation hard wireless RFID transponder with a radiation hard memory that stores a unique identifier. The radiation hard wireless RFID transponder may preferably transmit and/or receive signals in a relatively low radio frequency range, below that of conventional RFID transponders.

It may be advantageous if attachment structures that attach RFID transponder, other wireless transponder and/or integrated circuits to medical procedures objects are also radiation hard and/or composed of materials that withstand elevated heat or temperatures, elevated pressures, and/or combinations of elevated heat or temperatures and pressures commonly experienced during sterilization procedures.

In use on medical procedure sponges, the RFID transponder, other wireless transponder or integrated circuit may be retained in a pouch. The pouch may be closed or sealed via a weld (e.g., heat weld, RF weld) and/or via one or more stitches (e.g., sewn thread), or via one or more staples to retain the RFID transponder, other wireless transponder and/or integrated circuit in an interior of the pouch. The pouch may be attached to gauze or a sponge via a weld (e.g., heat weld, RF weld) and/or via one or more stitches. The pouch is preferably made of a material that withstands elevated temperatures, elevated pressures, and/or combinations of elevated temperatures and elevated pressures commonly employed in sterilization of objects for use in medical procedures, for example sterilization of gauze or sponges. The pouch is preferably made of a radiation hard material that withstands (essentially unaffected) by exposure to ionizing radiation (e.g., X-ray, Gamma ray radiation), particularly doses and durations of ionizing radiation employed in sterilization of objects for use in medical procedures, for example sterilization of gauze or sponges.

Likewise, material that closes or seals the pouch and/or that attaches the pouch to the gauze or sponge, is preferably made of a material that withstands elevated temperatures, elevated pressures, and combinations of elevated temperatures and elevated pressures commonly employed in sterilization of objects for use in medical procedures, for example sterilization of gauze or sponges. Likewise, material that closes or seals the pouch and/or that attaches the pouch to the gauze or sponge, is preferably made of a radiation hard material that withstands (essentially unaffected) by exposure to ionizing radiation (e.g., X-ray, Gamma ray radiation), particularly doses and durations of ionizing radiation employed in sterilization of objects for use in medical procedures, for example sterilization of gauze or sponges.

Gauze may be folded to position or space the pouch, RFID transponder, other wireless transponder and/or integrated circuit on one or more interior folds or portions of a plurality of folds or portions, inwardly of a pair of outermost folds, portions or layers of a sponge.

Sponges may optionally include one or more pieces of a radio-opaque material, to facilitate detection using medical imaging (e.g., ray-tech, X-ray). For example, one or more threads of radio-opaque material may be woven, knitted or attached to the gauze at one, two or more distinct locations. For instance, a first set of radio-opaque threads may extend across a width of the gauze or sponge at a first location, and a second set of radio-opaque threads may extend across the width of the gauze or sponge at a second location, spaced from the first location along a length of the gauze or sponge.

Gauze may be folded to position or space the radioopaque material on one or more interior folds or portions of a plurality of folds or portions, inwardly of a pair of outer-most folds, portions or layers of a sponge. Such may facilitate detection of closely spaced sponges, for example when verifying a total number of sponges in a packet or package of sponges, for instance during manufacturing or packaging.

On use on medical procedure instruments, the RFID transponder, other wireless transponder or integrated circuit may be attached via a variety of attachment structures. Attachment structures may, for example, include adhesive, epoxy or potting materials. The attachment structures may, for example, include one or more clamps, for instance with a spring or other bias member, or with a fastener, for instance a threaded fastener, with or without a nut or similar member. The attachment structure may comprise a housing, which may clamp or otherwise attach to the RFID transponder, other wireless transponder or integrated circuit. Where the medical procedure instrument is made of metal, the attachment structure may position the RFID transponder, other wireless transponder or integrated circuit at least or more 2 centimeters from metal.

The attachment structure is preferably made of a material that withstands elevated temperatures, elevated pressures, and/or combinations of elevated temperatures and elevated pressures commonly employed in sterilization of objects for use in medical procedures, for example sterilization of instruments or tools. The attachment structure is preferably made of a radiation hard material that withstands (essentially unaffected) by exposure to ionizing radiation (e.g., Gamma radiation), particularly doses and durations of ionizing radiation employed in sterilization of objects for use in medical procedures, for example sterilization of gauze or sponges.

Gauze and sponges, and associated pouches, RFID transponders, other wireless transponders, and integrated circuits will typically undergo on a single sterilization procedure. In contrast, medical procedure tools may be used repeatedly in two or more medical procedures, going through a sterilization procedure prior to each medical procedure. Thus, materials intended for use with gauze or sponges might be less robust with respect to the rigors experienced during sterilization as compared to those used for durable medical tools (e.g., scalpel, forceps, clamps).

The various materials preferably retain structural and functional integrity when exposed to heat, pressure, combinations of heat and pressure, and/or ionizing radiation. As used herein, radiation hard refers to any material that maintains its structural and functional integrity under dosages of radiation commonly used in sterilizing that particular medical procedure object to which the material is attached.

The various materials preferably retain structural and functional integrity at least at temperatures equal to 121 degrees Centigrade, or more preferably at least at temperatures equal to 130 degrees Centigrade, or even more preferably at least at temperatures equal to 136 degrees Centigrade, or most preferably at least at temperatures equal to, or greater than, 150 degrees Centigrade.

The RFID transponder, other RF transponder and/or integrated circuit retains structural and functional integrity at least at temperatures equal to 121 degrees Centigrade, or more preferably at least at temperatures equal to 130 degrees Centigrade, or even more preferably at least at temperatures equal to 136 degrees Centigrade, or most preferably at least at temperatures equal to, or greater than, 150 degrees Centigrade.

The attachment structure retains structural and functional integrity at least at temperatures equal to 121 degrees Centigrade, or more preferably at least at temperatures equal to 130 degrees Centigrade, or even more preferably at least at temperatures equal to 136 degrees Centigrade, or most preferably at least at temperatures equal to, or greater than, 150 degrees Centigrade, at or greater than 1 atmosphere. Thus, any material that forms the attachment structure that attaches to a sponge, including a pouch, thread, adhesive, or weld, retains structural and functional integrity, including for instance adhesive integrity at one or more of 121 degrees Centigrade, 130 degrees Centigrade, 136 degrees Centigrade, or 150 degrees Centigrade. Likewise, any material that forms the attachment structure that attaches to an instrument or tool, including a housing, adhesive, epoxy, potting material or weld, retains structural and functional integrity, including for instance adhesive integrity at one or more of 121 degrees Centigrade, 130 degrees Centigrade, 136 degrees Centigrade, or 150 degrees Centigrade.

The various materials preferably retain structural and functional integrity at least at ionizing radiation dosages of between approximately 8 and 15 kilogray (kGy), or more preferably between approximately 25 and 40 kGy, or even more preferably between approximately 50 and 100 kGy.

The RFID transponder, other RF transponder and/or integrated circuit retains structural and functional integrity at least at ionizing radiation dosages of between approximately 8 and 15 kilogray (kGy), or more preferably between approximately 25 and 40 kGy, or even more preferably between approximately 50 and 100 kGy, for from approximately 1 minute to 12 minutes.

The attachment structure retains structural and functional integrity at least at least at ionizing radiation dosages of between approximately 8 and 15 kGy, or more preferably between approximately 25 and 40 kGy, or even more preferably between approximately 50 and 100 kGy, for from approximately 1 minute to 12 minutes. Thus, any material that forms the attachment structure that attaches to a sponge, including a pouch, thread, adhesive, or weld, retains structural and functional integrity, including for instance adhesive integrity at least at ionizing radiation dosages of between approximately 8 and 15 kGy, or more preferably between approximately 25 and 40 kGy, or even more preferably between approximately 50 and 100 kGy, for from approximately 1 minute to 12 minutes. Likewise, any material that forms the attachment structure that attaches to an instrument or tool, including a housing, adhesive, epoxy, potting material or weld, retains structural and functional integrity, including for instance adhesive integrity at least at ionizing radiation dosages of between approximately 8 and 15 kGy, or more preferably between approximately 25 and 40 kGy, or even more preferably between approximately 50 and 100 kGy, for from approximately 1 minute to 12 minutes. Radiation sterilization of medical products is regulated under ISO 11137 (2006) part 1, part 2 and part 3.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 5A is a top view of an attachment structure that comprises a pouch, the pouch which holds or carries a presence transponder and an RFID transponder, according to one illustrated embodiment, each of the attachment structure and wireless transponders which maintain structural and functional integrity under sterilization procedures and conditions.

FIG. 5B is an exploded isometric view of the pouch of FIG. 5A.

FIG. 5C is first and second exploded side views of the pouch of FIGS. 5A and 5B.

DETAILED DESCRIPTION

In the following description, certain specific details are set forth in order to provide a thorough understanding of various disclosed embodiments.

However, one skilled in the relevant art will recognize that embodiments may be practiced without one or more of these specific details, or with other methods, components, materials, etc. In other instances, well-known structures associated with transmitters, receivers, or transceivers, and types of objects employed in medical procedures, for instance sponges, gauze or other absorbent objects, or instruments such as clips, clamps, forceps, scalpels, endoscopes, have not been shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

For ease of understanding, a clinical environment (e.g., surgical environment) will be used as an example environment for detecting objects but such should not be considered limiting. The structures and methods described herein may be employed in other clinical environments, for example labor and delivery rooms, physician offices, emergency rooms, etc.

Figure 1A:
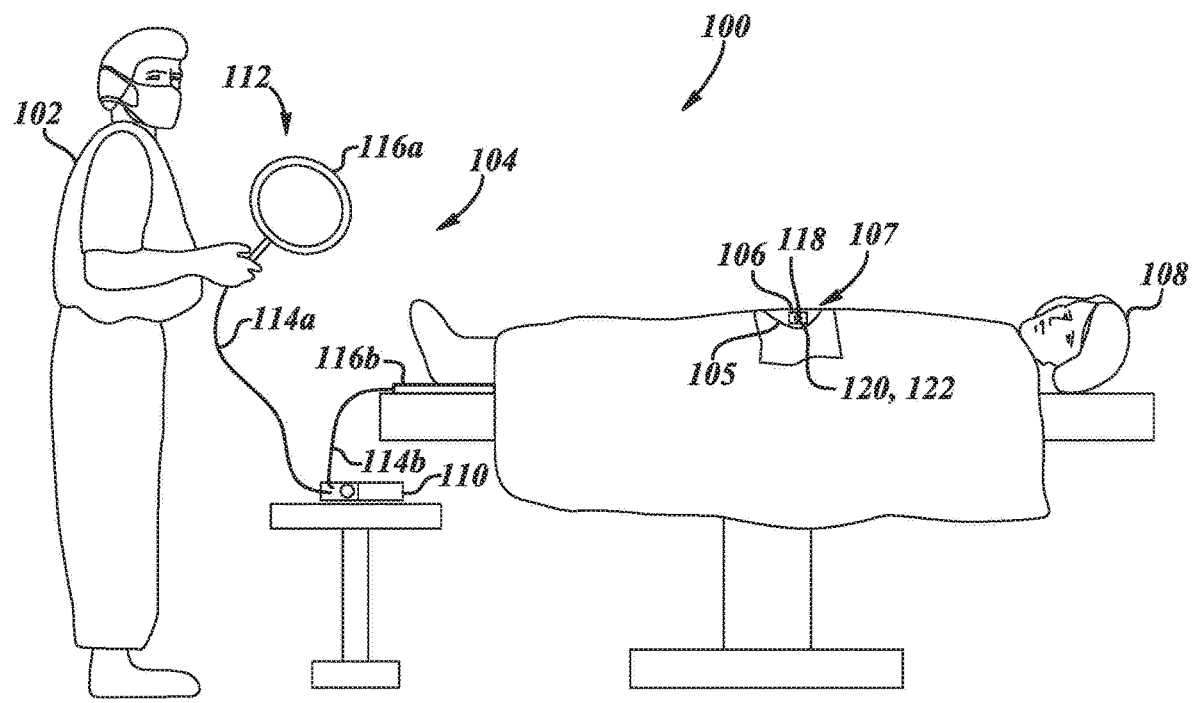
FIG. 1A is a schematic diagram illustrating a clinical or surgical environment where a medical provider uses an interrogation and detection system to detect a wirelessly detectable medical procedure object in a patient, according to one illustrated embodiment.

FIG. 1A shows a clinical or surgical environment 100 in which medical procedures are performed, for example an operating room, clinician's office, labor and delivery room, examination room, patient room or other environments in which medical procedures may be performed.

A medical provider 102 operates an identification and detection system 104 to ascertain that wirelessly detectable medical procedure objects 106 are not unintentionally left in a cavity or opening (e.g., wound, surgical incision, orifice) 105 in a body 107 of a patient 108. For example, the identification and detection system 104 may interrogate or excite wireless (e.g., radio frequency or microwave frequency) transponders 120, 122 (FIG. 1B) attached to a medical procedure object, and detect a response therefrom. The wireless transponders may take the form of radio frequency identification (RFID) transponders 120 (FIG. 1B), which store and/or return a unique identifier in response to an interrogation signal. Additionally, or alternatively, the wireless transponders may take the form of LC resonant circuit transponders 122 (FIG. 1B), which do not store or return unique identifiers and hence are denominated as "dumb" transponders 122.

Referring again to FIG. 1A, the identification and detection system 104 includes a controller 110, and one or more antennas 112 a, 112 b coupled to the controller 110 by one or more communication paths, for example a coaxial cable 114 a, 114 b. The antenna 112 a may take the form of a hand-held wand 116 a. In some implementations, the hand-held antenna 112 a is sized to fit at least partially in the cavity or opening 105. Additionally or alternatively, the antenna 112 b may take the form of mat 116 b or be incorporated into a bed or table 116 c. In some implementations, the antenna 112 b may include a plurality of coils, each extending across a width of the mat 116 b or table 116 c, and sequentially arranged along at least a portion of a length of the mat 116 b or table 116 c to allow scanning of most or all of the patient 108.

The controller 110 causes the antennas 112 a, 112 b to emit one or more wireless interrogation or excitation signals in one or more frequency bands, receives response signals to such interrogation or excitation signals from one or more wirelessly detectable medical procedure objects 106 via the antennas 112 a, 112 b. The controller 110 autonomously confirms that no wirelessly detectable medical procedure objects 106 are unintentionally left or retained in the body 107 based at least in part on the received response signals.

In particular, the antennas 112 a, 112 b can emit a first interrogation signal in a first frequency range and receive the first response signal from the RFID transponder 120. The console can decode the identifier encoded in the response signal(s), and/or update a list or database accordingly (e.g., check in, check out, count in, count out). The antennas 112 a, 112 b can further emit a second excitation or interrogation signal in a second frequency, receive the second response signal from the presence or dumb transponder 122, and receive a response signal, receipt of which is indicative of a presence of a presence of a wireless detectable medical procedure object 106 in the body 107.

Specific details of components of the antennas 112 a, 112 b are not discussed herein to not unnecessarily obscure the description of the embodiments. Components configured for emission of the interrogation signals and for receiving the first and second response signals can be selected from any suitable scanning technology, including, but not limited to, the detection device disclosed in U.S. Pat. No. 6,026,818, to Blair et al.; U.S. Pat. No. 7,696,877, to Barnes et al.; and U.S. Patent Publication No. 2013/0016021 by Blair, each of which are incorporated herein by reference.

Furthermore, in some implementations, the controller 110 of the interrogation device or assembly includes an interface that displays the name of the wirelessly detectable medical procedure objects 106 as the identification and detection system 104 scans the wirelessly detectable medical procedure objects 106. For example, the interface may display an accounting or inventory or list of sponges, gauzes, padding, hemostats, clips, clamps, forceps, scissors, scalpels, or other surgical or clinical tools or accessories, or any other wirelessly detectable medical procedure objects 106, for an expedient accounting of the wirelessly detectable medical procedure objects 106 being used during a particular clinical procedure.

When using RFID transponders 120, the identification and detection system 104 may interrogate the RFID transponders 120 before or at a start of a medical procedure, populating a list or database of wirelessly detectable medical procedure objects 106 by counting in or checking in each wirelessly detectable medical procedure object 106 based on unique identifiers returned from RFID transponders 120 attached to respective ones of the wirelessly detectable medical procedure objects 106. The identification and detection system 104 may interrogate the RFID transponders 120 after or at an end of a medical procedure, comparing against the list or database of wirelessly detectable medical procedure objects 106 by counting out or checking out each object based on unique identifiers returned from RFID transponders 120 attached to respective ones of the wirelessly detectable medical procedure objects 106.

When using LC resonant or dumb transponders 122, the identification and detection system 104 may interrogate or otherwise excite the dumb transponders 122 during a medical procedure, for instance just prior to closing of a wound or surgical opening. The identification and detection system 104 may determine the presence or absence of wirelessly detectable medical procedure objects 106 in, or on, a patient 108, for example in or on a surgical site, procedure site, area, cavity, opening, or orifice 105.

The wirelessly detectable medical procedure object 106 may take a variety of forms of medical procedure objects, with one or more transponders physically attached thereto. For example, the medical procedure objects 106 may take the form a durable or reusable medical procedure object, for instance an instrument or tool useful in performing medical procedures, for instance surgical or labor and delivery (L&D) procedures. For instance, the medical procedure object 106 may take the form of scalpels, scissors, forceps, hemostats, dilators, needles, a drill bit, clips and/or clamps or other clinically, medically or surgically useful objects. Also for example, the medical procedure objects 106 may take the form of accessories and/or disposable objects, for instance surgical sponges, gauze and/or padding. The surgical sponges, gauze and/or padding may be, as examples, 2 inches by 2 inches, 4 inches by 4 inches, 12 inches by 12 inches, or other sizes. Such dimensions may refer to the surgical sponges, gauze and/or padding as folded or otherwise packaged.

According to an aspect of the present disclosure, the wirelessly detectable medical procedure object 106 comprises a medical procedure object tagged, carrying, attached or otherwise coupled to a one or more wireless transponders 120, 122 via one or more attachment structures 118.

Figure 1B:
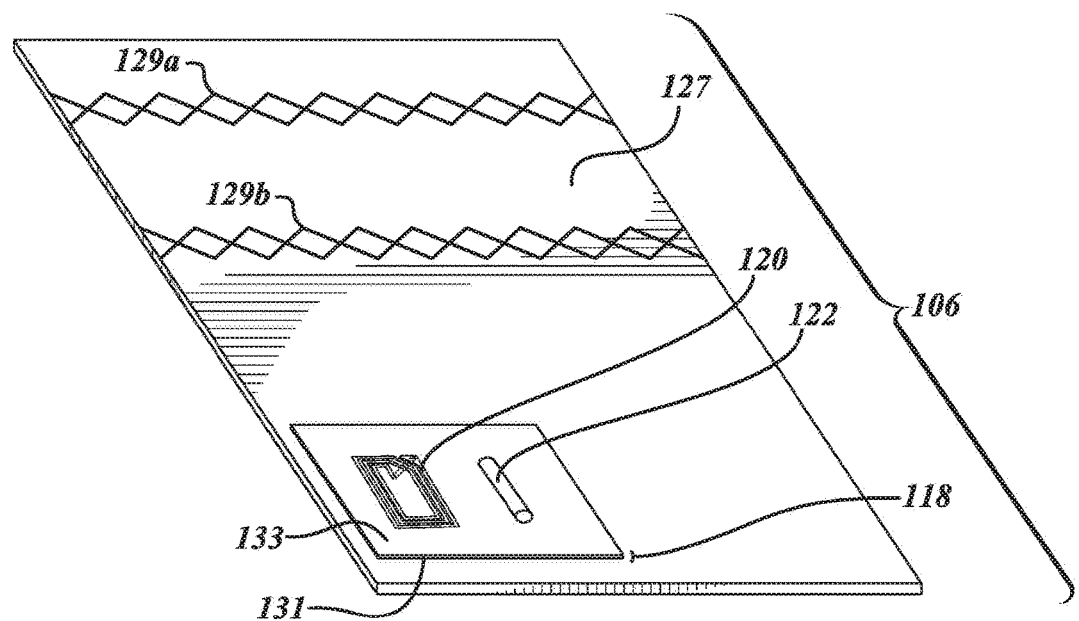
FIG. 1B is an isometric view of a medical procedure object tagged with a wirelessly detectable transponder to form a wirelessly detectable medical procedure object, according to one illustrated embodiment, the transponder which maintains structural and functional integrity under sterilization procedures and conditions, for instance when exposed to ionizing radiation at sterilization dosages for the medical procedure object and/or elevated temperatures and/or pressures according to sterilization protocols for the medical procedure object.

In particular, referring now to FIG. 1B, one or more wireless transponders 120, 122 is physically coupled to or otherwise physically associated with each medical procedure object by an attachment structure 118 to create or form a wirelessly detectable medical procedure object 106, for use within the clinical or surgical environment 100. The one or more wireless transponders can receive and respond to wireless signals. For example, in some implementations, a radio frequency identification (RFID) transponder 120, when interrogated, wirelessly returns a first response signal that contains unique identification information. Alternatively or additionally, a presence transponder 122, when excited at a resonance frequency or interrogated, wirelessly returns a second response signal that does not contain identification information.

Thus, in some implementations, the medical provider 102 can operate the identification and detection system 104 to confirm that wirelessly detectable medical procedure objects 106 where not unintentionally left behind in the patient 108. For example, the identification and detection system 104 may autonomously determine the presence or absence of wirelessly detectable medical procedure object 106 through wireless interrogation of the presence or dumb transponder 122. Also for example, the identification and detection system 104 may autonomously obtain identification information through wireless interrogation of the RFID transponder 120, counting or checking in and counting or checking out each wirelessly detectable medical procedure object 106 for a given medical procedure.

In some implementations, respective interrogation or excitation of and response by the presence transponder 122 and the RFID transponder 120 can occur in two different frequency ranges. For example, the frequency range associated with excitation of and response by the presence or dumb transponder 122 can include lower frequencies than the frequency range associated with interrogation of and response by the RFID transponder 120. Such lower frequencies may enable superior transmission of signals through bodily tissues or other obstacles including membranes, skin, flesh, etc. Thus, in some implementations, excitation of, and response by, the presence transponder 122 is possible at larger physical distances than interrogation of and response by the RFID transponder 120.

The RFID transponder 120 includes an integrated circuit electrically coupled to an antenna. The RFID transponder 120 may be relatively small, such as, for example, approximately 12 millimeters in diagonal.

In some implementations, the antenna can include an inductive winding such as a conductive wire wound about a core. The core can be fabricated from a ferrite rod. The inductive winding is electrically coupled to an integrated circuit. In other implementations, the antenna includes a conductive trace or other structures. The RFID transponder 120 may be an active device that includes a local consumable power source such as a battery, or alternatively may be a passive device that relies on energy harvested or derived from the interrogation signal to power the RFID transponder 120.

The RFID transponder 120 may have physical characteristics that accommodate or withstand the rigors of sterilization procedures or protocols.

For example, the RFID transponder 120 takes the form of a radiation hard RFID transponder, that is an RFID transponder with a radiation hard or hardened RFID integrated circuit and/or front end. Radiation hard RFID transponders 120 retain structural and functional integrity to ionizing radiation at least at ionizing radiation dosages of between approximately 8 and 15 kilogray (kGy), or more preferably between approximately 25 and 40 kGy, or even more preferably between approximately 50 and 100 kGy, for from approximately 1 minute to 12 minutes.

The RFID transponder 120 may preferably take the form of a write once, read many times of memory circuit, which may advantageously enhance the radiation hardness of the RFID transponder 120. Additionally or alternatively, the RFID transponder's 120 integrated circuit may be formed on an insulating substrate, for instance using silicon on insulator or silicon on sapphire substrates. The substrate may be selected to have a relatively wide band gap, for example employing gallium nitride of silicon carbide. Additionally or alternatively, the RFID transponder's 120 integrated circuit may employ bipolar integrated circuits or bipolar junction transistors, in lieu of field effect transistors (FETs). Additionally or alternatively, the RFID transponder's 120 integrated circuit may include SRAM in lieu of DRAM. Additionally or alternatively, the RFID transponder's 120 integrated circuit may be encapsulated with a shielding, for instance using a borophophosilicate glass with depleted boron, to harden the integrated circuit from X-ray and Gamma ray radiation. Additionally or alternatively, the RFID transponder's 120 integrated circuit may include firmware or software mechanisms to correct for errors introduced by exposure to ionizing radiation. For instance, the integrated circuit may implement error correction, for example via parity checking, can employ redundant logic elements, and/or radiation hardened latches.

Materials to fabricate the RFID transponder and associated integrated circuit are selected accordingly. For example, material selected to serve as a substrate may be a polymer, so should be a polymer that withstands the aforementioned dosages of the ionizing radiation, as well as any temperatures and/or pressures that the RFID transponder may be subjected to in undergoing sterilization. Many polymers are resistant to radiation doses of up to approximately 25 KGy, for example poly methyl methacrylate, polyurethane or thermosetting polyurethane, polyolefins and other thermoplastics, polymer blends containing aromatic groups such as polystyrene or containing nanoparticles or antioxidants.

Also for example, the RFID transponder 120 retains structural and functional integrity at temperatures and/or pressures specified by sterilization procedures or protocols. For instance, the RFID transponder 120 retains structural and functional integrity at least at temperatures equal to 121 degrees Centigrade, or more preferably at least at temperatures equal to 130 degrees Centigrade, or even more preferably at least at temperatures equal to 136 degrees Centigrade, or most preferably at least at temperatures equal to, or greater than, 150 degrees Centigrade, at or greater than 1 atmosphere. Materials to fabricate the RFID transponder and associated integrated circuit are selected accordingly. For example, material selected to serve as a substrate may be a polymer, so should be a polymer that withstands the aforementioned temperatures and pressures, as well as dosages of the ionizing radiation. For example, various thermosetting polymers may be employed, or silicon or sapphire.

The RFID transponder 120 is operable to transmit (e.g., via active radiation of the antenna) a first response signal that contains identification information, in response to receiving an interrogation signal in a first frequency range. The first response signal encodes the identification information or identifier stored by the integrated circuit. As such, the RFID transponder 122 may be denominated as a "smart" transponder.

The identification information included in the first response signal may be a unique identifier (i.e., unique over a set of all otherwise identical RFID transponders 120). Alternatively, the identifier may not be unique, for example, a set of RFID transponders 120 may each have the same identifier. Even where the identifier is unique, some portion of the identification information or some other identification information may not be unique, for example, a portion representing a manufacturer, a lot, or a type, may be shared between transponders 120 from the same manufacturer, lot or of the same type. In some implementations, the identification information can be associated with a type of the wirelessly detectable medical procedure object 106 or an attribute thereof. For example, the identification information can be linked to the type or attribute using a database, lookup table, or other data structure that cross-references unique identifiers with the type or attribute.

Alternatively, in implementations where the integrated circuit of the RFID transponder 120 has read and write capability, the identification information can include the desired attribute, pre-stored or written onto the integrated circuit, and directly convey the pre-stored attribute via the first response signal.

Furthermore, in some implementations, the RFID transponder 120 is a printable and/or ultra-low-cost RFID transponder 120 that is not necessarily intended to maintain functionality beyond a single use of the wirelessly detectable medical procedure object 106, and hence exposure to only one or two sterilization cycles. Such may be common with disposables, for instance sponges, gauze or pads, as opposed to more durable instruments or tools Recognition of the limited service life of a medical procedure object may advantageously permit inclusion of a lower-cost RFID transponder 120 with lower resistance to sterilization than might otherwise be used for more durable instruments or tools.

The presence or dumb transponder 122 may be constructed in various manners. For example, the presence or dumb transponder 122 may include a ferrite rod with a conductive coil wrapped about an exterior surface thereof to form an inductor, and a capacitor coupled to the conductive coil to form a series circuit. The conductive coil may, for example, take the form of a spiral wound conductive wire with an electrically insulative sheath or sleeve. For example, the inductive coil and capacitor may together form an inductive/capacitance (L/C) tank circuit. Additional details about types of transponders may be found in U.S. Provisional Patent Application Ser. No. 60/811,376 filed Jun. 6, 2006 (published as U.S. Patent Publication No. 2007/0285249) and U.S. Provisional Patent Application Ser. No. 60/892,208, filed Feb. 28, 2007 (now U.S. Pat. No. 8,710, 957), both of which are incorporated herein by reference.

The presence or dumb transponder 122 may have physical characteristics that accommodate or withstand the rigors of sterilization procedures or protocols.

For example, the presence or dumb transponder 122 takes the form of a radiation hard LC resonant transponder, that is an LC resonant transponder with a radiation hard or hardened circuitry (e.g., capacitor). Radiation hard presence or dumb transponders 122 retain structural and functional integrity to ionizing radiation at least at ionizing radiation dosages of between approximately 8 and 15 kilogray (kGy), or more preferably between approximately 25 and 40 kGy, or even more preferably between approximately 50 and 100 kGy, for from approximately 1 minute to 12 minutes. The radiation hard presence or dumb transponders 122 integrated circuit may, for example, be encapsulated with a shielding, for instance using a borophophosilicate glass with depleted boron, to harden the integrated circuit from X-ray and Gamma ray radiation.

Also for example, the presence or dumb transponders 122 retains structural and functional integrity at temperatures and/or pressures specified by sterilization procedures or protocols. For instance, the presence or dumb transponders 122 retains structural and functional integrity at least at temperatures equal to 121 degrees Centigrade, or more preferably at least at temperatures equal to 130 degrees Centigrade, or even more preferably at least at temperatures equal to 136 degrees Centigrade, or most preferably at least at temperatures equal to, or greater than, 150 degrees Centigrade, at or greater than 1 atmosphere. Ferrite and many metal, as well as silicon can withstand these temperatures and pressures.

The presence transponder 122 is operable to transmit (e.g., via radiation of the inductive coil) a second response signal, in response to receiving an excitation signal in a second frequency range. The second response signal does not include any unique identifying information and, therefore, indicates only that the presence transponder 122 is present. As such, the presence transponder 122 may be denominated as a "dumb" transponder. However, in some implementations, presence transponder 122 provides superior response strength through bodily tissue relative to the RFID transponder 120.

The presence transponder 122 may be relatively small, for example approximately 5-10 millimeters long with a diameter of about 1-4 millimeters. In at least some embodiments, an encapsulant advantageously protects the transponder from the ambient environment, for instance from forces, shock, pressure, heat, ionizing radiation, and/or fluids, such as bodily fluids.

In some implementations, the presence transponder 122 includes a dumbbell-shaped ferrite rod having broad end portions and a narrow intermediate portion. The broad end portions may provide capacitive functionality. In other implementations, the presence transponder 122 may be shaped as a fusiform-shaped object, with truncated ends.

In further implementations, the wirelessly detectable medical procedure object 106 includes at least one directional antenna. For example, in some implementations, an active antenna element of the RFID transponder 120 forms at least a portion of the directional antenna. In some implementations, the wirelessly detectable medical procedure object 106 does not include the presence or dumb transponder 122. Particular example structures and arrangements of the wirelessly detectable medical procedure object 106 are discussed further below with reference to the Figures that follow.

FIG. 1B depicts the wirelessly detectable medical procedure object 106 as comprising an RFID transponder 120, dumb transponder 122 and attachment structure 118 that physically couples the RFID transponder 120 and dumb transponder 122 to an external surface of a medical procedure object in the form of a piece of gauze 127. Notably, the piece of gauze 127 may then be folded and/or stitched to form a pad or sponge. In particular, the piece of absorbent material or gauze 127 may be folded or otherwise manipulated such that the RFID transponder 120 and/or dumb transponder 122 are no longer carried on an external surface of the resulting pad or sponge and/or externally visible. As an example, the piece of absorbent material or gauze 127 may be folded into quadrants to provide, for example, a folded sponge, gauze, or padding that has four discernable layers. As a result of the folding, the RFID transponder 120 and/or dumb transponder 122 may be carried internally between layers of the piece of absorbent material or gauze 127 and visible only upon unfolding of the piece of absorbent material or gauze 127. Likewise, one or more pieces of radio-opaque material (e.g., radio opaque threads, barium threads) 129 *a*, 129 *b*, may be positioned such that when the piece of absorbent material or gauze 127 is folded, the pieces of radio-opaque material 129 *a*, 129 *b* preferably appear on inner layers, folds or portions of the resulting pad or sponge, spaced inwardly and between a pair of outermost layers, folds or portions of the resulting pad or sponge.

The attachment structure 118 may include or consist of an adhesive layer 131 that directly or indirectly physically couples the RFID transponder 120 and/or dumb transponder 122 to the piece of absorbent material or gauze 127 or other medical procedure object (e.g., sponge, instrument, tool). The adhesive layer 131 may retain structural and adhesive integrity at least at temperatures equal to 121 degrees Centigrade, 130 degrees Centigrade, 132 degrees Centigrade, 136 degrees Centigrade, and/or 150 degrees Centigrade, or higher.

For example, the adhesive layer 131 may not melt or otherwise liquefy and may maintain functional adhesion at temperatures less than or equal to 121 degrees Centigrade, 130 degrees Centigrade, 132 degrees Centigrade, 136 degrees Centigrade, and/or 150 degrees Centigrade or higher.

As an example, the adhesive layer 131 may be a hot melt adhesive layer positioned between the medical procedure object (e.g., gauze 127) and the RFID transponder 120 and/or dumb transponder 122 or a pouch or substrate 133 which carries the RFID transponder 120 and/or dumb transponder 122. In such implementations, the RFID transponder 120 and/or dumb transponder 122 may be directly or indirectly physically coupled to the medical procedure (e.g., surgical, labor and delivery), for example piece of gauze 127 by causing the temperature of at least a portion the hot melt adhesive layer to exceed a melting point temperature associated with the hot melt adhesive layer, thereby causing such portion to at least in part melt. For example, such may be performed using an RF welding machine, planar heat pressing machine, hot-air welding machine, or laminator. Alternatively, the wirelessly detectable medical procedure object 106 may be baked (e.g., in a chamber) or exposed to various other techniques for applying heat and/or pressure at desired locations. Generally, the melting point temperature will be at least greater than 121 degrees Centigrade, but may be other temperatures.

Thus, for example, in contrast to an epoxy that is applied in liquid form and then cured, the adhesive layer 131 of the attachment structure 118 may be a pre-formed solid layer that is positioned or laid between the RFID transponder 120 and/or dumb transponder 122 and the medical procedure object (e.g., sponge 127). The adhesive layer 131 may then be caused to at least in part melt and then re-solidify, thereby engaging the remainder of the RFID transponder 120 and/or dumb transponder 122 with the medical procedure object (e.g., sponge 127) and resulting in direct or indirect physical coupling therebetween.

In some implementations, the hot melt adhesive layer 131 is a high temperature hot melt adhesive layer (i.e., a hot melt adhesive layer that has a relatively high melting point temperature) 131. For example, the hot melt adhesive layer 131 may have a melting point temperature of greater than 121 degrees Centigrade, greater than 130 degrees Centigrade, greater than 132 degrees Centigrade, or greater than 136 degrees Centigrade. As another example, the hot melt adhesive layer 131 may have a melting point temperature of about 150 degrees Centigrade or higher.

More particularly, according to an aspect of the present disclosure, the hot melt adhesive layer 131 may have a melting point temperature greater than a sterilization temperature associated with one or more sterilization procedures. For example, the hot melt adhesive layer 131 may have a melting point temperature greater than a steam temperature at which a volume of steam is maintained during one or more steam-based sterilization procedures. For example, two common steam-based sterilization techniques use a volume of steam respectively maintained at 121 degrees Centigrade (250 degrees Fahrenheit) and 132 degrees Centigrade (270 degrees Fahrenheit). The hot melt adhesive layer 131 may have a melting point temperature greater than one or both of such temperatures.

Further, certain sterilization procedures may be performed with pressure conditions greater than 1 atmosphere. The hot melt adhesive layer 131 may any of the melting point temperature characteristics described herein at such pressure conditions.

In some implementations, the adhesive layer 131 and optional pouch or substrate 133 is biocompatible, permitting use of the wirelessly detectable medical procedure object 106 in vivo. In some implementations, the adhesive layer 131 is an adhesive web film. In some implementations, the adhesive layer 131 is a thermal lamination film. The adhesive layer 131 may be a meltable plastic layer, such as, for example, a thermoplastic layer.

In some implementations, the adhesive layer 131 may be a thermosetting plastic layer that has an initial cure temperature at which the thermosetting plastic layer cures. For example, the initial cure temperature may be less than 130 degrees Centigrade. Subsequent to curing, the thermosetting plastic layer may retain structural and adhesive integrity at least at temperatures less than or equal to 121, 130, 132, 136, and/or 150 degrees Centigrade or higher.

In some implementations, the adhesive layer 131 may be a heat-activated adhesive layer. Alternatively or additionally, the adhesive layer 131 may be a pressure-activated adhesive layer 131 or a pressure-sensitive adhesive layer 131. Alternatively or additionally, the adhesive layer 131 may be a water-activated adhesive layer 131.

Additionally or alternatively, the adhesive layer, and optional pouch or substrate 133, may be radiation hard or hardened. For example, the adhesive layer 131, and optional pouch or substrate 133, retains structural and functional (e.g., adhesive) integrity to ionizing radiation at least at ionizing radiation dosages of between approximately 8 and 15 kilogray (kGy), or more preferably between approximately 25 and 40 kGy, or even more preferably between approximately 50 and 100 kGy, for from approximately 1 minute to 12 minutes.

The adhesive layer 131 may include at least one of thermoplastic polyurethane, silicone, polyamide, polyethersulfone, polyethylene, polypropylene, and ethylene vinyl acetate, with or without aromatic groups, nanoparticles or antioxidants.

As one example method of operation, a user, such as the medical provider 102, can scan the patient 108 to detect presence or absence of wirelessly detectable medical procedure objects 106 within the patient 108 through wireless interrogation of one or more presence or dumb transponders 122. For example, such interrogation of the presence or dumb transponders 122 can occur at a first physical distance. Upon detecting the presence of a wirelessly detectable medical procedure object 106 within the patient 108, the medical provider 102 can immediately scan the region of detection to wirelessly interrogate one or more RFID transponders 120 and thereby identify the one or more objects 106 that remain. For example, such interrogation of the RFID transponders 120 can occur at a second physical distance that is less than the first physical distance. Having obtained the identity of the wirelessly detectable medical procedure object 106, the medical provider 102 can make informed decisions with respect to handing of the wirelessly detectable medical procedure object 106. For example, the medical provider 102 can remove wirelessly detectable medical procedure object 106 prior to closing a wound or opening in the body 107 of a patient 108.

As another example, upon removing the wirelessly detectable medical procedure object or objects 106 from the body 107 of the patient 108, and with all the wirelessly detectable medical procedure objects 106 laid out in an area after a medical procedure (e.g., surgery, labor and delivery) and before closing the surgical site, wound, incision, orifice or area 105, the medical provider 102 can scan the present objects 106 to ensure that all the objects 106 that were present before surgery, are now present and outside of the body 107 of the patient 108 after or just prior to completion of the medical procedure. For example, the medical provider 102 can interrogate the RFID transponder 120 of each wirelessly detectable medical procedure object 106 to identify all which are present. The wirelessly detectable medical procedure objects 106 which are identified as present can be compared to a list or record of wirelessly detectable medical procedure objects 106 identified and logged or recorded prior to use within the surgical or clinical environment to detect any discrepancies (i.e., missing objects).

As yet another example method of operation, one or more RFID transponders 120 for one or more wirelessly detectable medical procedure objects 106 may be interrogated at a conclusion of or during a manufacturing process, for example, to ensure that an appropriate number of objects 106 are included in a shipping tote or other package. Upon entry into and use of the wirelessly detectable medical procedure objects 106 within the clinical or surgical environment, the RFID transponders 120 may or may not degrade. However, the medical provider 102 may still interrogate one or more presence transponders 122 to advantageously detect presence or absence of wirelessly detectable medical procedure objects 106 within the patient 108.

Accordingly, the wirelessly detectable medical procedure objects 106 of the present disclosure provide the capability to efficiently detect a presence or absence of medical procedure related objects in or on the body of the patient 108, and the capability to conduct an inventory after or just prior to completion of the medical or clinical procedure (e.g., surgery, labor and delivery) to ensure all wirelessly detectable medical procedure objects 106 present at the start of a clinical procedure (e.g., surgery, labor and delivery) are present and accounted for at the end of the medical or clinical procedure, without the use of multiple separately affixed optically-readable symbols (e.g., barcode symbols) and without the need to conduct a manual count by highly trained and highly paid personnel.

Further, although a human patient 108 is illustrated, the described interrogation and detection system 104 may similarly be used on animals or inanimate subjects.

Figure 2A:
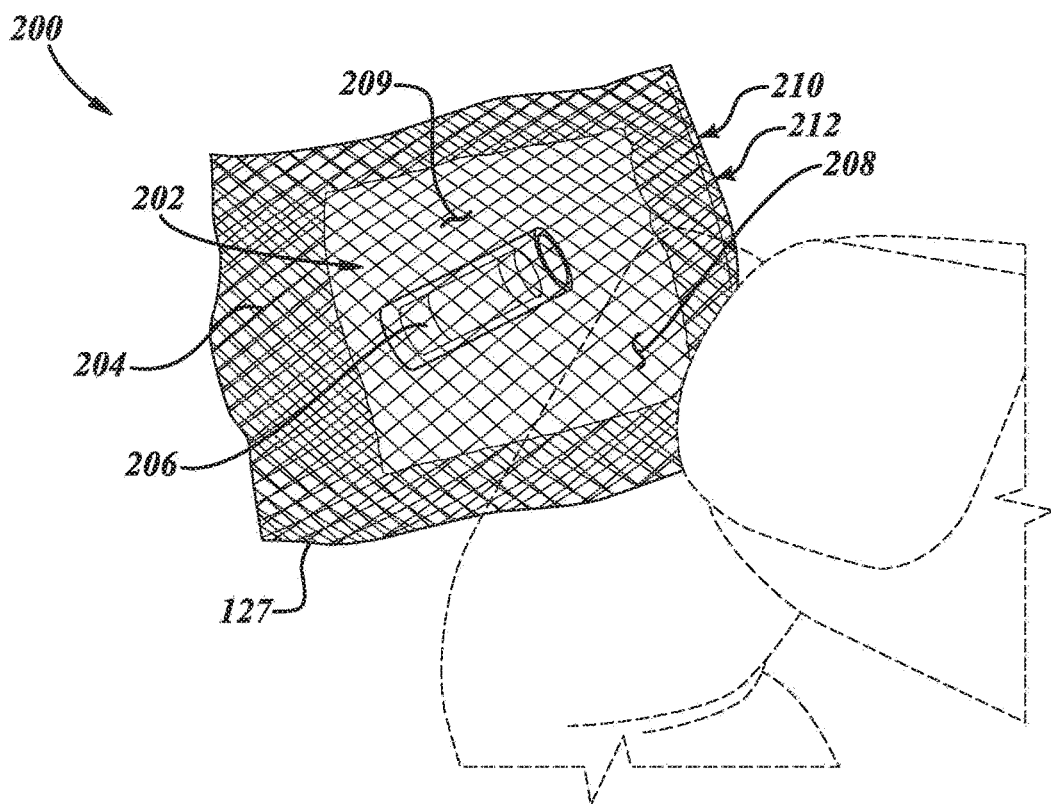
FIG. 2A is a front view of a portion of a wirelessly detectable medical procedure object comprising a medical procedure object in the form of a piece of absorbent material, gauze or sponge, and a pouch that holds or carries a presence or "dumb" transponder, according to one illustrated embodiment, the pouch and the wireless transponder(s) which each maintain structural and functional integrity when subjected to sterilization procedures and conditions.

FIG. 2A shows a portion of a wirelessly detectable medical procedure object 200 in the form of a piece of absorbent material, gauze or sponge 227 and a pouch 202 that includes at least one wireless transponder, for instance a presence or dumb transponder 206, according to one illustrated embodiment. In particular, in some implementations, the attachment structure 118 comprises a pouch 202 that holds or otherwise retains a presence or dumb transponder 206 within an interior cavity of the pouch 202. The pouch 202 is physically coupleable to a medical procedure object, for example a piece of absorbent material, gauze or sponge 127, to form the wirelessly detectable medical procedure object 200.

In some implementations, the presence or dumb transponder 206 is freely movable within the interior cavity of the pouch 202. Such may advantageously allow folding, stretching, compression, twisting, or other physical manipulation of the piece of absorbent material, gauze, sponge 127 or other medical procedure object without causing damage to the presence or dumb transponder 206. For example, the presence or dumb transponder 206 freely moves within the pouch 202 to an advantageous position experiencing reduced forces. Likewise, the free-floating presence or dumb transponder 206 does not inhibit folding, stretching, compression, twisting, or other physical manipulation of the piece of absorbent material, gauze or sponge 127 or other object, which may be necessary for successfully performing the medical (e.g., surgical, labor and delivery) procedure.

The pouch 202 includes at least a first flexible layer 208 that forms the interior cavity 209 of the pouch 202. For example, the first flexible layer 208 can be physically coupled to a surface of an medical procedure object, e.g., a piece of absorbent material, gauze or sponge 127 to form the interior cavity therebetween. As another example, as shown in FIG. 2A, the pouch 202 includes a second flexible layer 210 opposite the first flexible layer 208 and physically coupled to the first flexible layer 208 to form the interior cavity 209 therebetween.

In the illustrated embodiment, the pouch 202 further includes an adhesive layer 212 positioned opposite the second flexible layer 210 from the first flexible layer 208. The adhesive layer 212 may be physically coupled to one or both of the first flexible layer 208 and the second flexible layer 210. Furthermore, in some implementations, the adhesive layer 212 physically couples the pouch 202 to a piece of absorbent material, gauze or sponge 127 or other object.

The pouch 202, including the adhesive layer 212, may retain structural and adhesive integrity at least at ionizing radiation dosages of between approximately 8 and 15 kilogray (kGy), or more preferably between approximately 25 and 40 kGy, or even more preferably between approximately 50 and 100 kGy.

Additionally or alternatively, the pouch, including the adhesive layer 212, may retain structural and adhesive integrity at least at temperatures equal to 121, 130, 132, 136, and/or 150 degrees Centigrade or higher. For example, the adhesive layer 212 may not melt or otherwise liquefy and may retain adhesion to the first flexible layer 208, second flexible layer 210 and/or the piece of the absorbent material, gauze or sponge 127 at temperatures less than or equal to 121, 130, 132, 136, and/or 150 degrees Centigrade or higher.

In some implementations, the adhesive layer 212 is physically coupled to at least a portion of a first surface of the second flexible layer 210 and the first flexible layer 208 is physically coupled to at least a portion of a second surface of the second flexible layer 210 that is opposite the first surface. In particular, in some implementations, the adhesive layer 212 is physically coupled to at least the first surface of the second flexible layer 210 about a perimeter of the interior cavity and the first flexible layer 208 is physically coupled to at least the second surface of the second flexible layer 210 about the perimeter of the interior cavity 209. In such implementations, the interior cavity 209 may be formed between the first flexible layer 208 and the second flexible layer 210, as illustrated, or may be formed between the second flexible layer 210 and the adhesive layer 212.

In other implementations, the adhesive layer 212 is continuously physically coupled to at least the first surface of the second flexible layer 210 and the first flexible layer 208 is physically coupled to at least the second surface of the second flexible layer 210 about the perimeter of the interior cavity. In such implementations, the interior cavity 209 may be formed between the first flexible layer 208 and the second flexible layer 210, as illustrated.

In yet other implementations, the pouch 202 includes the adhesive layer 212, but does not include the second flexible layer 210. In such implementations, the first flexible layer 208 is physically coupled to the adhesive layer 212. For example, the first flexible layer 208 may be physically coupled to the adhesive layer 212 at least about the perimeter to form the interior cavity 209 therebetween.

In some implementations, a heat or radio frequency (RF) weld 204 physically couples the first flexible layer 208 to one or both of the second flexible layer 210 and the adhesive layer 212. For example, the heat or RF weld 204 extends around a perimeter of the interior cavity 209 and closes the presence transponder 206 within the pouch 202. A width of the heat or RF weld 204 can be varied to balance various objectives such as a strength of weld 204 and a size of the pouch 202. Alternatively or additionally to the heat or RF weld 204, adhesives, stitches, clamps, fasteners, or other securement or fastening structures can physically couple the first flexible layer 208 to the medical procedure object (e.g., piece of absorbent material, gauze or sponge 127) or the second flexible layer 210.

The first and/or second flexible layers 208 and 210 may be fabric laminates or other materials. For example, the first and/or second flexible layers 208 and 210 may be one or more of thermoplastic polyurethane (TPU) and nylon fabric; polyvinyl chloride (PVC) impregnated fabric; layer(s) of PVC, TPU, PET, PETG, LDPE, EVA, open celled polyurethanes, or nylon; other fabrics (e.g., cotton, polyester, leather, vinyl, polyethylene, and blended fabrics); other plastics; or combinations thereof. The flexible layers 208 and 210 are typically relatively thin and may be absorbent or non-absorbent. In some implementations, the flexible layers are of material suitable to prevent entry of fluids into the interior cavity of the pouch 202 (e.g., due to a water-proof or water-resistant coating). Thus, the first and/or second flexible layers 208 and 210 may be soft, pliable, and resistant to ripping or tearing.

In one particular example, the first flexible layer 208 includes a first layer of TPU and a first layer of nylon fabric. The second flexible layer 210 includes a second layer of TPU and a second layer of nylon fabric. For example, the first and second layers of TPU may respectively be located interior relative to the first and second layers of nylon fabric. In other words, the first and second layers of TPU may contact each other and may form an interior surface of the interior cavity of the pouch 202 while the first and second layers of nylon fabric are respectively carried by respective exterior surfaces of the first and second layers of TPU that are opposite to the interior cavity. Such may advantageously allow the first and second layers of TPU to more completely melt together or otherwise physically couple to each other when the RF weld 204 is generated. However, in other implementations, the first and second layers of nylon fabric may be located interior relative to the first and second layers of TPU or may be embedded within the first and second layers of TPU.

In some implementations, the adhesive layer 212 is a hot melt adhesive layer 212. In such implementations, the pouch 202 may be constructed at least in part by causing the temperature of at least a portion the hot melt adhesive layer 212 to exceed a melting point temperature associated with the hot melt adhesive layer 212, thereby causing such portion to at least in part melt. For example, such may be performed using an RF welding machine, planar heat pressing machine, hot-air welding machine, or laminator. Alternatively, the pouch 202 may be baked (e.g., in a chamber) or exposed to various other techniques for applying heat and/or pressure at desired locations. Generally, the melting point temperature will be at least greater than 130 degrees Centigrade.

Thus, for example, in contrast to an epoxy that is applied in liquid form and then cured, the adhesive layer 212 may be a pre-formed solid layer that is positioned or laid adjacent to the first and/or the second flexible layers 208 and 210 and then caused to at least in part melt and then re-solidify, thereby engaging the first and/or the second flexible layers 208 and 210 and resulting in physical coupling therewith. For example, in some implementations, the second layer 210 is a porous fabric and the adhesive layer 212 melts through the pores of the fabric to engage the first flexible layer 208. Such may result in physical coupling of the first flexible layer 208 to the second flexible layer 210 by way of the adhesive layer 212. Further, in some implementations, the adhesive layer 212 may be caused to at least in part melt, engage a piece of a medical procedures object (e.g., piece of absorbent material, gauze or sponge 127) or other medical procedure object, and then re-solidify, resulting in physical coupling of the pouch 202 to the medical procedure object such as piece of absorbent material, gauze or sponge 127.

In some implementations, the hot melt adhesive layer 212 is a high temperature hot melt adhesive layer 212 (i.e., a hot melt adhesive layer that has a relatively high melting point temperature). For example, the hot melt adhesive layer 212 may have a melting point temperature of greater than 121, 130, 132, or 136 degrees Centigrade. As another example, the hot melt adhesive layer 212 may have a melting point temperature of about 150 degrees Centigrade or higher. Additionally or alternatively, the hot melt adhesive layer 212 may be a radiation hot melt adhesive that retains structural and functional (e.g., adhesiveness) integrity to ionizing radiation at least at ionizing radiation dosages of between approximately 8 and 15 kilogray (kGy), or more preferably between approximately 25 and 40 kGy, or even more preferably between approximately 50 and 100 kGy, for from approximately 1 minute to 12 minutes, or even longer.

More particularly, according to an aspect of the present disclosure, the hot melt adhesive layer 212 may have a melting point temperature greater than a sterilization temperature associated with one or more sterilization procedures. For example, the hot melt adhesive layer may have a melting point temperature greater than a steam temperature at which a volume of steam is maintained during one or more steam-based sterilization procedures. For example, two common steam-based sterilization techniques use a volume of steam respectively maintained at 121 degrees Centigrade (250 degrees Fahrenheit) and 132 degrees Centigrade (270 degrees Fahrenheit). The hot melt adhesive layer 212 may have a melting point temperature greater than one or both of such temperatures.

Further, certain sterilization procedures may be performed with pressure conditions greater than 1 atmosphere. The hot melt adhesive layer 212 may any of the melting point temperature characteristics described herein at such pressure conditions.

Also for example, a common sterilization technique uses ionizing radiation (e.g., X-ray, Gamma ray). The hot melt adhesive layer 212 may retain structural integrity and its adhesive properties at suitable dosages, for instance approximately 25 kGy.

In some implementations, the adhesive layer 212 is biocompatible, permitting use of the wirelessly detectable object in vivo. In some implementations, the adhesive layer 212 is an adhesive web film. In some implementations, the adhesive layer 212 is a thermal lamination film. The adhesive layer 212 may be a meltable plastic layer, such as, for example, a thermoplastic layer.

In some implementations, the adhesive layer 212 may be a thermosetting plastic layer that has an initial cure temperature at which the thermosetting plastic layer cures. For example, the initial cure temperature may be less than 130 degrees Centigrade. Subsequent to curing, the thermosetting plastic layer may retain structural and adhesive integrity at least at temperatures less than or equal to 121, 130, 132, 136, and/or 150 degrees Centigrade or higher. Subsequent to curing, the thermosetting plastic layer may retain structural and adhesive integrity at least at ionizing radiation dosages of between approximately 8 and 15 kilogray (kGy), or more preferably between approximately 25 and 40 kGy, or even more preferably between approximately 50 and 100 kGy, for from approximately 1 minute to 12 minutes, or even longer.

In some implementations, the adhesive layer 212 may be a heat-activated adhesive layer. Alternatively or additionally, the adhesive layer 212 may be a pressure-activated adhesive layer or a pressure-sensitive adhesive layer. Alternatively or additionally, the adhesive layer 212 may be a water-activated adhesive layer.

The adhesive layer 212 may include at least one of thermoplastic polyurethane, silicone, polyamide, polyethersulfone, polyethylene, polypropylene, and ethylene vinyl acetate. These polymers may, for example, comprise a polymer blend, for instance containing aromatic groups such as polystyrene or containing nanoparticles or antioxidants.

In one particular example pouch 202, the first flexible layer 208 is a nylon layer; the second flexible layer 210 is a TPU layer; and the adhesive layer 212 is a hot melt adhesive layer. In some implementations, the pouch 202 does not include the adhesive layer 212.

Figure 2B:
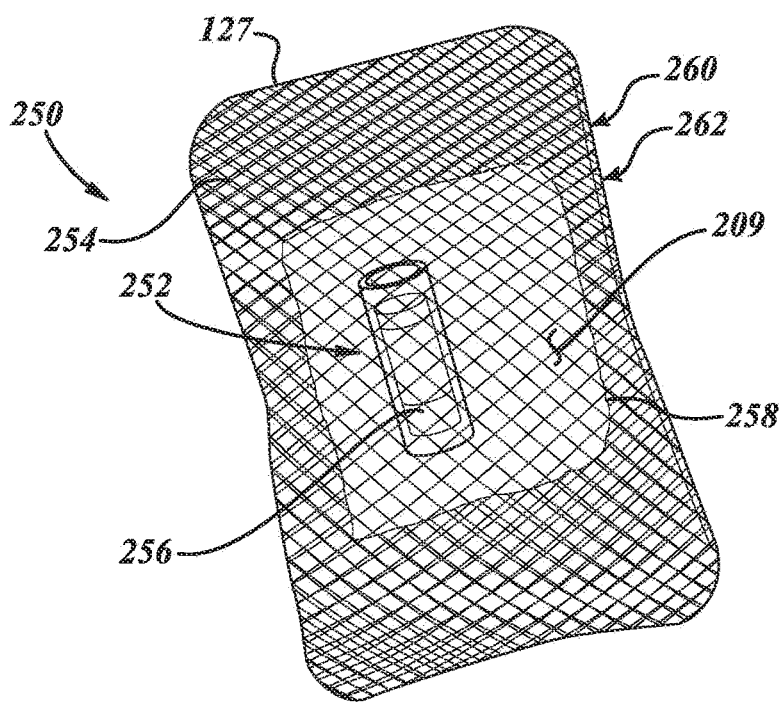
FIG. 2B is a front view of a wirelessly detectable medical procedure object comprising a medical procedure object and another pouch that includes a presence or "dumb" transponder, according to one illustrated embodiment, the pouch and the transponder each of which maintain structural and functional integrity when subjected to sterilization procedures and conditions.

FIG. 2B shows a portion of a wirelessly detectable medical procedure object 250 in the form of a piece of absorbent material, gauze or sponge 127 and a pouch 252 that includes at least one wireless transponder, for instance a presence or dumb transponder 256, according to one illustrated embodiment. The pouch 252 is physically coupleable to a medical procedure object, for example a piece of absorbent material, gauze or sponge 127, to form the wirelessly detectable medical procedure object 250.

In particular, pouch 252 includes a first flexible layer 258 physically coupled to a second flexible layer 260 by an RF weld 254. The presence or dumb transponder 256 is received and freely movable within an interior cavity 209 formed between the first and second flexible layers 258 and 260. In particular, the RF weld 254 extends around a perimeter of the interior cavity 209 and closes the presence or dumb transponder 256 within the interior cavity 209 of the pouch 252. The pouch 252 is physically coupleable to a medical procedure object, for example a piece of absorbent material, gauze or sponge 127. For example, the pouch 252 includes an adhesive layer 262 positioned opposite the second flexible layer 260 from the first flexible layer 258. The adhesive layer 262 may be a hot melt adhesive layer that is meltable to physically couple the pouch 252 to a piece of absorbent material, but that has a melting point temperature greater than one or more sterilization temperatures at which common sterilization techniques are performed, thereby permitting the pouch 252 to remain physically coupled to the piece of absorbent material through one or multiple sterilization cycles. The adhesive layer 262 may also advantageously retain structural and adhesive integrity at least at ionizing radiation dosages of between approximately 8 and 15 kilogray (kGy), or more preferably between approximately 25 and 40 kGy, or even more preferably between approximately 50 and 100 kGy, for from approximately 1 minute to 12 minutes, or even longer.

Figure 3:
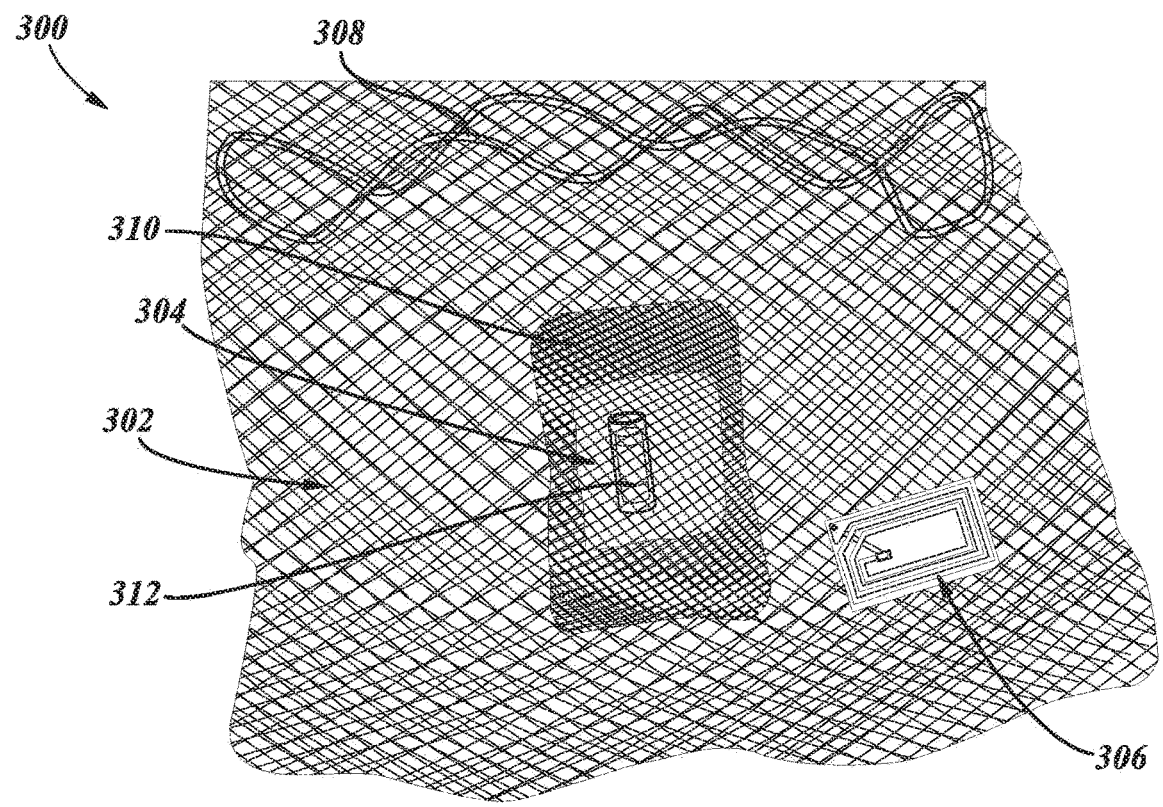
FIG. 3 is a front view of a portion of a wirelessly detectable medical procedure object comprising an RFID transponder and presence or dumb transponder coupled to a medical procedure object via an attachment structure, according to one illustrated embodiment, the medical procedure object in the form of a piece of absorbent material, gauze or sponge, each of the medical procedure object, transponders, and attachment structure which maintain structural and functional integrity under sterilization procedures and conditions.

FIG. 3 shows a wirelessly detectable medical object 300, which comprises a piece of absorbent material, gauze or sponge 302 with an RFID transponder 306 and a presence or dumb transponder 312 physically coupled thereto via at least one attachment structure, for example a pouch 304, according to one illustrated embodiment.

More precisely, a pouch 304 is physically coupled to the piece of absorbent material 302. The pouch 304 includes a first flexible layer physically coupled to a second flexible layer to form an interior cavity therebetween. The flexible layers may the same as or similar to layers 208 and 210 discussed with reference to FIG. 2A, so are not specifically called out in FIG. 3. The pouch 304 may include an adhesive layer that physically couples the pouch 304 to the piece of absorbent material 302. The adhesive layer may be the same as or similar to layer 212 discussed with reference to FIG. 2A. In some implementations, the pouch 304 does not include the adhesive layer.

A presence transponder 312 is retained and freely movable within the interior cavity of the pouch 304. An RF weld 310 physically couples the first flexible layer to the second flexible layer. In some implementations, the RF weld 310 further physically couples the pouch 304 to the piece of absorbent material, gauze or sponge 302. In other implementations, an additional RF weld or other attachment structure (e.g. adhesive layer) physically couples the pouch 304 to the piece of absorbent material, gauze or sponge 302.

As shown in FIG. 3, the RFID transponder 306 is physically coupled to the piece of absorbent material, gauze or sponge 302 separately from the pouch 304. Adhesives, stitching, clamping, fasteners, heat sealing, RF welding, or other attachment structure physically couple the RFID transponder 306 the piece of absorbent material, gauze or sponge 302. In some implementations, a radiopaque thread or object 308 is woven into or otherwise physically coupled to the piece of absorbent material, gauze or sponge 302, as well.

Furthermore, although FIG. 3 depicts pouch 304 and RFID transponder 306 as physically coupled to and visible upon an external surface of the piece of absorbent material, gauze or sponge 302, in some implementations, the piece of absorbent material, gauze or sponge 302 is folded or otherwise manipulated such that the pouch 304 and RFID transponder 306 are internally carried between layers or folds or portions of the piece of absorbent material, gauze or sponge 302.

Figure 4:
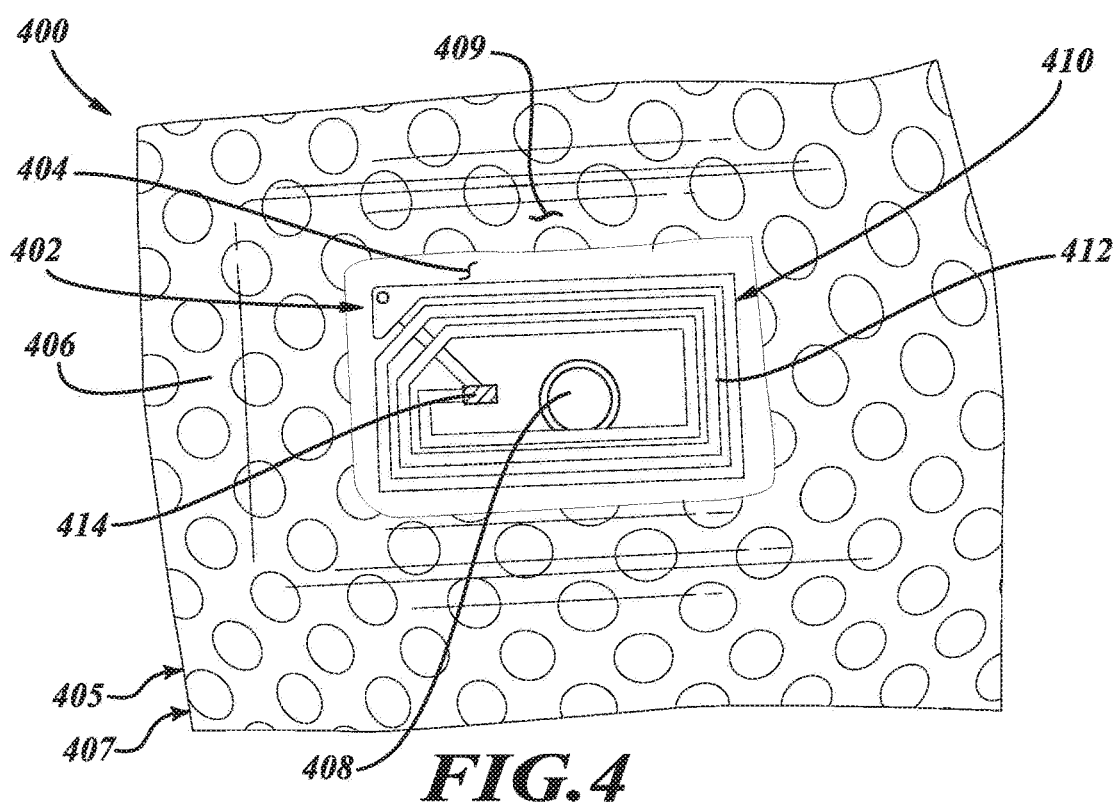
FIG. 4 is a front view of an attachment structure that comprises a pouch, the pouch which holds or carries a presence transponder freely movable within an interior cavity of the pouch and an RFID transponder, according to one illustrated embodiment, each of the attachment structure and wireless transponders which maintain structural and functional integrity under sterilization procedures and conditions.

FIG. 4 shows an attachment structure 400 that comprises a pouch 402. The pouch holds a presence or dumb transponder 408, freely movable within an interior cavity 409 of the pouch 402 and an RFID transponder 410 with an antenna trace 412, according to one illustrated embodiment.

The pouch 402 includes a first flexible layer 404 physically coupled to a second flexible layer 405 to form an interior cavity 409 therebetween. The flexible layers 404 and 405 may the same as or similar to layers 208 and 210 discussed with reference to FIG. 2A. The pouch 402 includes an adhesive layer 407 physically coupled to at least the second flexible layer 405. The adhesive layer 407 may be the same as or similar to adhesive layer 212 discussed with reference to FIG. 2A.

The presence transponder 408 is retained and freely movable within the interior cavity 409 of the pouch 402. In particular, an RF weld 406 physically couples the first flexible layer 404 to the second flexible layer 405 and closes or seals the presence or dumb transponder 408 within the interior cavity 409. The RFID transponder 410 includes an antenna trace 412 electrically coupled to a chip 414. An integrated circuit that stores identification information can form all or a portion of the chip 414.

All or a portion of the RFID transponder 410 can be embedded in and/or adhered to the first flexible layer 404. For example, in some implementations, the chip 414 is adhered to the first flexible layer 404 (e.g., adhered to a surface of the first layer 404 that faces the interior cavity 409) while the antenna trace 412 is embedded within the first flexible layer 404. In other implementations, the antenna trace 412 is printed or traced onto the first flexible layer 404 (e.g., onto an interior surface that faces the interior cavity). In yet other implementations, all or a portion of the RFID transponder 410 is embedded in and/or adhered to the second flexible layer 405.

In some implementations, at least a portion of the first flexible layer 404 and/or the second flexible layer 405 is a material that is absorbent but remains electrically insulative, thereby contributing to an absorbency of an attached piece of absorbent material without interfering with an ability of the antenna trace 412 to transmit a signal.

As the presence transponder 408 is freely movable within the interior cavity 409 of the pouch 402 and the RFID transponder 410 is embedded in and/or adhered to the first flexible layer 404, the presence transponder 408 is independently movable with respect to the RFID transponder 410. Furthermore, as shown in FIG. 4, in some implementations, care is taken to prevent the RF weld 406 from welding over and potentially damaging the antenna trace 412. In addition, in some implementations, the pouch 402 does not include the adhesive layer 407.

FIGS. 5A, 5B and 5C show a pouch 502 that holds a presence or dumb transponder 508 *b*, freely movable within an interior cavity 509 formed between a first flexible layer 504 *b* and a substrate 506 *b* of the pouch 502, according to one illustrated embodiment. An RFID transponder 512 *b* is adhered to the substrate 506 *b*.

An encapsulant 510 encapsulates the presence or dumb transponder 508 *b*. The encapsulant 510 may provide a shielding for the presence transponder 508 *b* or for a capacitor thereof to harden the presence transponder 508 *b* or capacitor with respect to X-ray and Gamma ray radiation. The encapsulant 510 may, for instance, comprise a borophosphosilicate glass with depleted boron.

The substrate 506 *b* can be a second flexible layer, a surgical procedure object, for instance a piece of absorbent material, gauze or sponge, or other substrates. In particular, the first flexible layer 504 *b* and the substrate 506 *b* may the same as or similar to layers 208 and 210 discussed with reference to FIG. 2A. In some implementations, an RF weld physically couples the first flexible layer 504 *b* to the substrate 506 *b*. In the illustrated embodiment, the pouch 502 further includes an adhesive layer 507 *b*. The adhesive layer 507 *b* may be the same as or similar to layer 212 discussed with reference to FIG. 2A. However, in some implementations, the pouch 502 does not include the adhesive layer 507 *b*.

FIG. 5C better illustrates the interior cavity 509 formed between the first flexible layer 504 *c* and the substrate 506 *c* of the pouch 502, according to one illustrated embodiment. As illustrated, the RFID transponder 512 *c* may be adhered to the substrate 506 *c* of the pouch 502. For example, in some implementations, some or all of the RFID transponder 512 *c* (e.g., a chip portion) is adhered to the substrate 506 *c* using adhesives or other securing means. In some implementations, some or all of the RFID transponder 512 c (e.g., an antenna portion) is printed onto or traced upon the substrate 506 c. The illustrated pouch 502 optionally includes an adhesive layer 507 c. The adhesive layer 507 c may take the form of previously described adhesives. For example, the adhesive layer 507 c may retain its structural and functional integrity when exposed to elevated temperatures and/or pressures and/or ionizing radiation dosages commonly employed during sterilization of objects to be used in medical applications, such as clinical or surgical procedures, as previously specified herein.

Figure 6A:
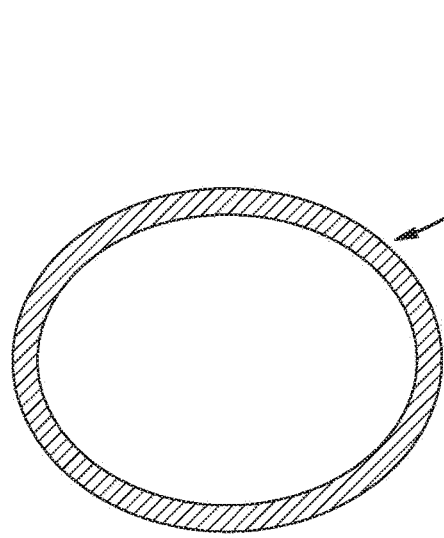
FIG. 6A is a top view of an attachment structure that comprises a pouch, the pouch which holds or carries a presence transponder and an RFID transponder, according to one illustrated embodiment, each of the attachment structure and wireless transponders which maintain structural and functional integrity under sterilization procedures and conditions.
Figure 6B:
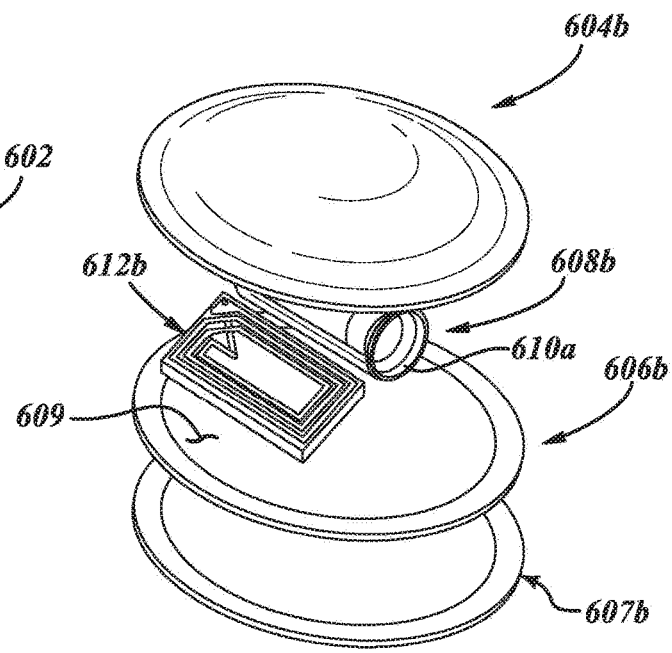
FIG. 6B is an exploded isometric view of the pouch of FIG. 6A.
Figure 6C:
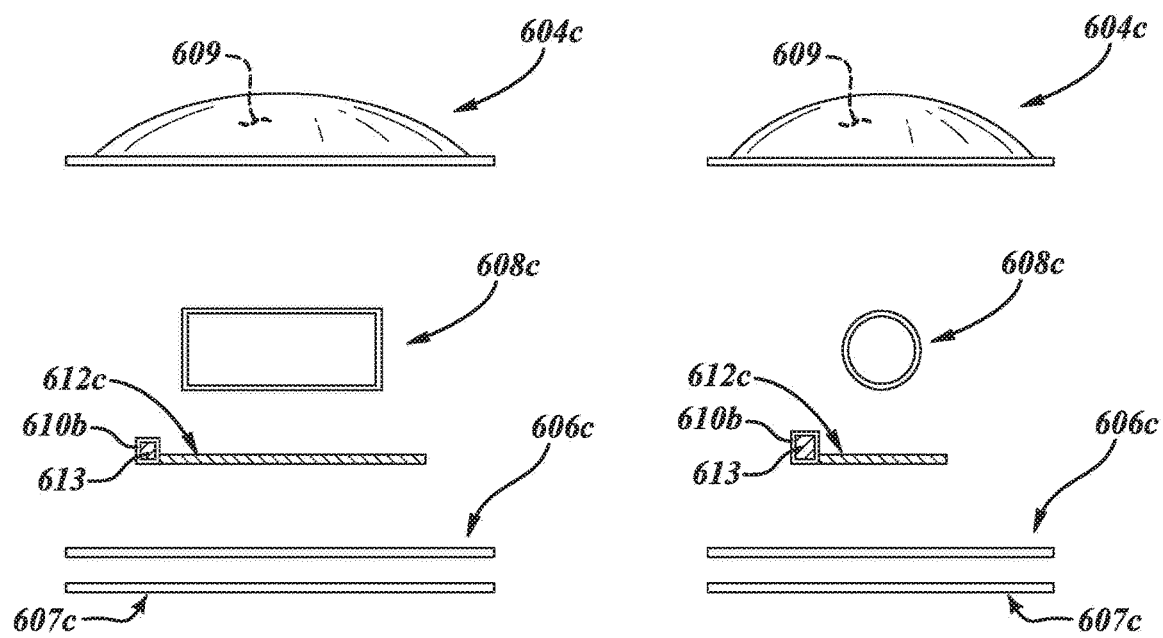
FIG. 6C is first and second exploded side views of the pouch of FIGS. 6A and 6B.

FIGS. 6A, 6B and 6C show a pouch 602 that holds a presence or dumb transponder 608 b and an RFID transponder 612 b freely movable within an interior cavity 609 formed between a first flexible layer 604 b and a substrate 606 b of the pouch 602, according to one illustrated embodiment. An encapsulant 610 a encapsulates the presence transponder 608 b. An encapsulant 610 b encapsulates the RFID transponder 612 b. The encapsulants 610 a, 610 b may provide a shielding for the presence transponder 508 b and RFID transponder 612 b, respectively or for a capacitor the presence transponder 508 b or integrated circuit 613 of the RFID transponder 612 b, to harden the presence transponder 508 b or capacitor and the RFID transponder 612 b or integrated circuit 613 with respect to X-ray and Gamma ray radiation. The encapsulant 610 a, 610 b may, for instance, comprise a borophophosilicate glass with depleted boron.

The substrate 606 b can be a second flexible layer, a surgical procedure object, for instance a piece of absorbent material, gauze or sponge, or other substrates. In particular, the first flexible layer 604 b and the substrate 606 b may the same as or similar to layers 208 and 210 discussed with reference to FIG. 2A. In some implementations, an RF weld physically couples the first flexible layer 604 b to the substrate 606 b. In the illustrated embodiment, the pouch 602 further includes an adhesive layer 607 b. The adhesive layer 607 b may be the same as or similar to layer 212 discussed with reference to FIG. 2A. However, in some implementations, the pouch 602 does not include the adhesive layer 607 b.

FIG. 6C better illustrates the interior cavity 609 formed between the first flexible layer 604 c and the substrate 606 c of the pouch, according to one illustrated embodiment. The illustrated pouch 602 includes the adhesive layer 607 c. As discussed above, the adhesive layer 607 b may retain structural and functional (e.g., adhesiveness) integrity when subjected to conditions associated with sterilization, for instance elevated temperature, pressure and/or ionizing radiation, as specified above.

Figure 7:
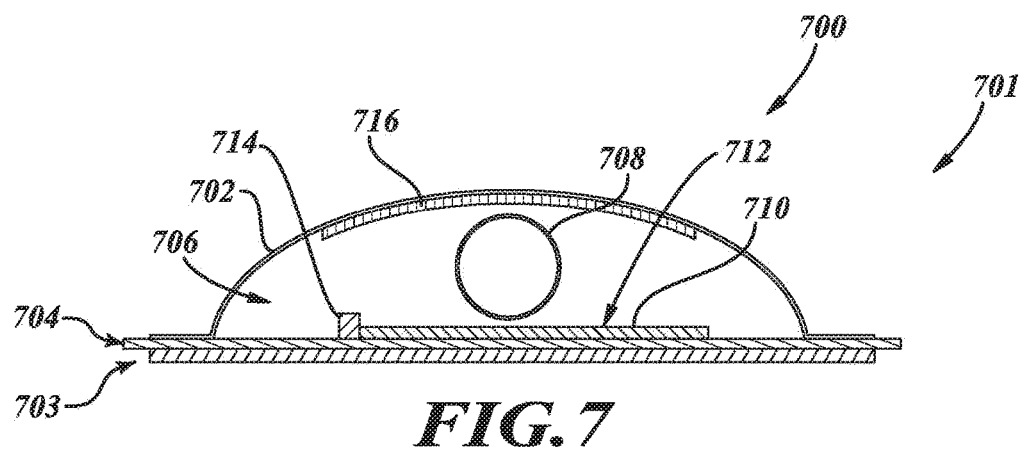
FIG. 7 is a cross-sectional diagram of an attachment structure in the form of a pouch that holds or carries a presence transponder, an RFID transponder and an optional a directional antenna formed on or within the pouch, according to one illustrated embodiment, all of which maintain structural and functional integrity under sterilization procedures and conditions.

FIG. 7 shows an attachment structure 700 in the form of a pouch 701 that carries or holds at least one wireless transponder (e.g., presence or dumb transponder 708, RFID transponder 710) and optionally a directional antenna formed on or contained within the pouch, according to one illustrated embodiment.

In particular, the pouch 701 includes a first flexible layer 702 physically coupled to a substrate 704 to form an interior cavity 706 therebetween. A presence or dumb transponder 708 is received and freely movable enclosed or retained within the interior cavity 706. The substrate 704 can be a second flexible layer, a surgical object such as a piece of absorbent material, or other substrates. In particular, the first flexible layer 702 and the substrate 704 may the same as or similar to layers 208 and 210 discussed with reference to FIG. 2A.

In the illustrated embodiment, the attachment structure 700 further includes an adhesive layer 703. The adhesive layer 703 may be the same as or similar to layer 212 discussed with reference to FIG. 2A. However, in some implementations, the wirelessly detectable object 700 does not include the adhesive layer 703.

The attachment structure 700 holds an RFID transponder 710 that includes at least one active antenna element 712 and an integrated circuit 714. For example, the integrated circuit 714 can actively drive or energize the active antenna element 712 of the RFID transponder 710 to transmit a signal. The RFID transponder 710 may be received and enclosed or retained within the interior cavity 706 of the pouch 701. The RFID transponder 710 may be freely movable within the interior cavity 706 of the pouch 701. Alternatively, the RFID transponder 710 may be secured or fixed within the interior cavity 706 of the pouch 701, for instance secured to the substrate 704 or first flexible layer 702, for instance via an adhesive. Alternatively, the RFID transponder 710 may form all or a portion of the pouch 701, for example forming a layer of the pouch 701, or being part of a lamination of layers that form a portion (e.g., substrate 704) the pouch 701.

The attachment structure 700 may further carry one or more passive antenna elements 716 (only one shown) that, together with the active antenna element 712, operates as a directional antenna. For example, the passive antenna element 716 and the active antenna element 712 may together operate as a Yagi antenna.

As shown in FIG. 7, the passive antenna element 716 can be a separate structure from the active antenna element 712 of the RFID transponder 710. However, in other implementations, the passive antenna element 716 and the active antenna element 712 may be included within a single integral structure. In some implementations, two or more passive antenna elements 716 act as a reflector element and a director element, respectively.

As shown in FIG. 7, the passive antenna element 716 may be adhered to or printed, deposited or otherwise formed upon an interior surface of the first flexible layer 702 that faces the interior cavity 706. However, in other implementations, the passive antenna element 716 may be at least partially embedded in the first flexible layer 702 or adhered to or printed, deposited or otherwise formed upon an exterior surface of the first flexible layer 702. The active antenna element 712 is adhered to or printed, deposited or otherwise formed upon an interior surface of the substrate 704 that faces the interior cavity 706. However, in other implementations, the active antenna element 712 may be at least partially embedded within the substrate 704 or adhered to or traced upon an exterior surface of the substrate 704.

In yet further implementations, the respective positions of the active antenna element 712 and the passive antenna element 716 may be opposite to those depicted in FIG. 7. That is, the passive antenna element 716 may be adhered to or embedded within the substrate 704 while the active antenna element 712 is adhered to or embedded within the first flexible layer 702.

All of the materials that form the attachment structure 700, as well as the presence or dumb transponder 708 and the RFID transponder 710 may retain their structural and functional integrity when exposed to elevated temperatures and/or pressures and/or ionizing radiation dosages commonly employed during sterilization of objects to be used in medical applications, such as clinical or surgical procedures, as previously specified herein. One or more components or structures may be protected or shielded, for instance by an encapsulant that retains its structural and functional integrity when exposed to elevated temperatures and/or pressures and/or ionizing radiation dosages commonly employed during sterilization of objects to be used in medical applications, such as clinical or surgical procedures, as previously specified herein.

Figure 8:
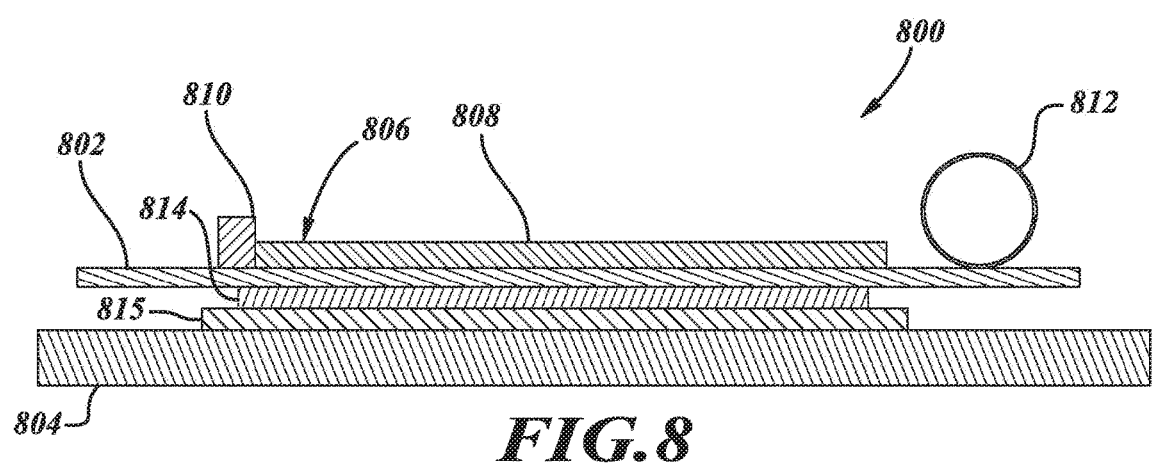
FIG. 8 is a cross-sectional diagram of an attachment structure that carries a presence or dumb transponder, an RFID transponder 806, and optionally a directional antenna, according to one illustrated embodiment, all of which maintain structural and functional integrity under sterilization procedures and conditions.

FIG. 8 shows an attachment structure 800 that carries at least one wireless transponder (e.g., presence or dumb transponder 812, RFID transponder 806) and optionally a directional antenna carried at least in part by a first substrate 802, according to one illustrated embodiment.

The attachment structure 800 is physically coupled to a medical procedure object, for instance a piece of absorbent material, gauze or sponge 804. The attachment structure 800 may, for example, include an adhesive layer 815, which may be positioned between and respectively physically coupled to the remainder of the attachment structure 800 and the piece of absorbent material, gauze or sponge 804. However, in some implementations, the attachment structure 800 does not include the adhesive layer 815.

The first substrate 802 may be a first flexible layer. For example, the first substrate 802 may be the same as or similar to layers 208 and 210 discussed with reference to FIG. 2A. The adhesive layer 815 may be the same as or similar to layer 212 discussed with reference to FIG. 2A.

The RFID transponder 806 includes an active antenna element 808 and an integrated circuit 810. For example, the integrated circuit 810 may selectively actively energize or otherwise cause the active antenna element 808 to radiate to transmit a signal. The attachment structure 800 may optionally carry or hold one or more passive antenna elements 814 (only one shown) that, together with the active antenna element 808, operates as a directional antenna. For example, the passive antenna element 814 and the active antenna element 808 may together operate as a Yagi antenna.

As shown in FIG. 8, the passive antenna element 814 is positioned between the first substrate 802 and the piece of absorbent material, gauze or sponge 804. For example, the passive antenna element 814 can be adhered to, printed, deposited or otherwise formed onto, or otherwise carried by one or both of the first substrate 802, the adhesive layer 815, and/or the piece of absorbent material, gauze or sponge 804. However, in other implementations, at least a portion of the passive antenna element 814 is embedded within or forms a portion of the first substrate 802 or the piece of absorbent material, gauze or sponge 804 or other medical procedure object (e.g., medical instrument, tool).

In yet further implementations, the respective positions of the active antenna element 808 and the passive antenna element 814 may be opposite to those depicted in FIG. 8. That is, the passive antenna element 814 may be adhered to or carried by a surface of the first substrate 802 that is opposite the piece of absorbent material, gauze or sponge 804 while the active antenna element 808 is positioned between the first substrate 802 and the piece of absorbent material, gauze or sponge 804.

While FIG. 8 depicts first substrate 802 as not contacting the piece of absorbent material, gauze or sponge 804 or the adhesive layer 815, in some implementations, the first substrate 802 is directly physically coupled to (e.g., by an heat or RF weld) the piece of absorbent material, gauze or sponge 804. Further, in some implementations, the presence dumb transponder 812 is omitted.

All of the materials that form the attachment structure 800, as well as the presence or dumb transponder 812 and the RFID transponder 806 may retain their structural and functional integrity when exposed to elevated temperatures and/or pressures and/or ionizing radiation dosages commonly employed during sterilization of objects to be used in medical applications, such as clinical or surgical procedures, as previously specified herein. One or more components or structures may be protected or shielded, for instance by an encapsulant that retains its structural and functional integrity when exposed to elevated temperatures and/or pressures and/or ionizing radiation dosages commonly employed during sterilization of objects to be used in medical applications, such as clinical or surgical procedures, as previously specified herein.

Figure 9:
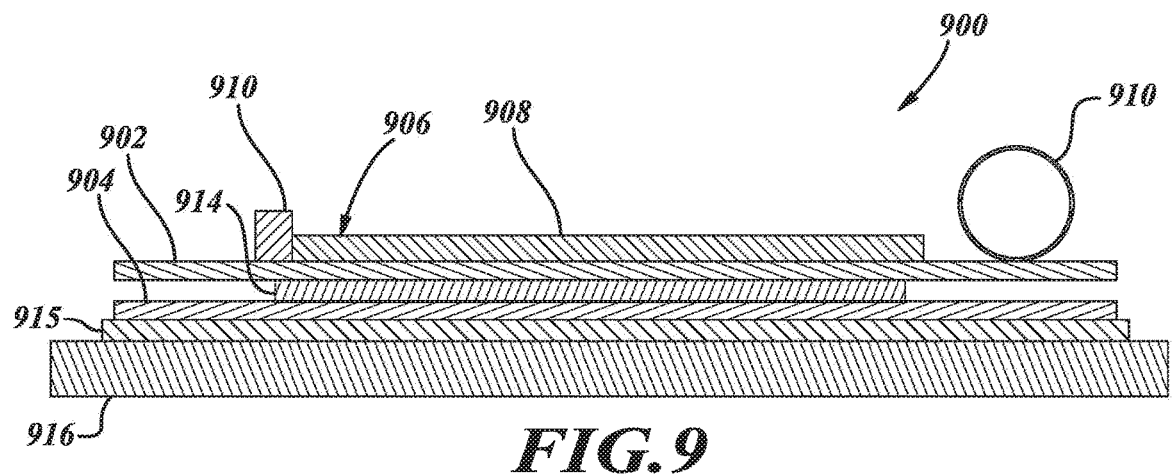
FIG. 9 is a cross-sectional diagram of an attachment structure that carries a presence or dumb transponder, an RFID transponder, and optionally a directional antenna, according to one illustrated embodiment, all of which maintain structural and functional integrity under sterilization procedures and conditions.

FIG. 9 shows an attachment structure 900 that carries at least one wireless transponder (e.g., presence or dumb transponder 910, RFID transponder 906) and optionally a directional antenna carried at least in part by a first substrate 902, according to one illustrated embodiment.

The attachment structure 900 is physically coupled to a medical procedure object, for instance a piece of absorbent material, gauze or sponge 916. The attachment structure 900 may, for example, include an adhesive layer 915, which may be positioned between and respectively physically coupled to the remainder of the attachment structure 900 and the piece of absorbent material, gauze or sponge 916. However, in some implementations, the attachment structure 900 does not include the adhesive layer 915.

An RFID transponder 906 and a presence or dumb transponder 910 are physically coupled to the first substrate 902 of the attachment structure 900. The attachment structure 900 further includes a second substrate 904. The first substrate 902 and/or the second substrate 904 may be flexible layers. For example, the first substrate 902 and/or the second substrate 904 may be the same as or similar to layers 208 and 210 discussed with reference to FIG. 2A. The adhesive layer 915 may be the same as or similar to adhesive layer 212 discussed with reference to FIG. 2A.

The RFID transponder 906 includes an active antenna element 908 and an integrated circuit 910. For example, the integrated circuit 910 may selectively actively energize or otherwise cause the active antenna element 908 to radiate to transmit a signal. The attachment structure 900 optionally carries or holds one or more passive antenna elements 914 (only one shown) that, together with the active antenna element 908, operates as a directional antenna. For example, the passive antenna element 914 and the active antenna element 908 may together operate as a Yagi antenna.

As shown in FIG. 9, the passive antenna element 914 is positioned between the first substrate 902 and the second substrate 904. For example, the passive antenna element 914 can be adhered to, printed, deposited or otherwise formed onto, or otherwise carried by one or both of the first substrate 902 and/or the second substrate 904. However, in other implementations, at least a portion of the passive antenna element 914 is embedded within or forms a portion of the first substrate 902 or the second substrate 904.

In yet further implementations, the respective positions of the active antenna element 908 and the passive antenna element 914 may be opposite to those depicted in FIG. 9. That is, the passive antenna element 914 may be adhered to or carried by a surface of the first substrate 902 that is opposite the second substrate 904 while the active antenna element 908 is positioned between the first substrate 902 and the second substrate 904. Further, in some implementations, one or more heat or RF welds or other securement structures (e.g., adhesive layer 915, stitches, staples) physically couple one or both of the first and second substrates 902 and 904 to the piece of absorbent material, gauze, sponge 916 or other medical procedure object which are used to perform medical procedures.

Furthermore, while FIG. 9 depicts first substrate 802 as not directly contacting the second substrate 904, in some implementations, the first substrate 902 is directly physically coupled to (e.g., by a heat or RF weld) the second substrate 904. Likewise, a heat or RF weld may physically couple the second substrate 904 to the piece of absorbent material, gauze or sponge 916 or other medical procedure object. Further, in some implementations, the presence or dumb transponder 910 is omitted.

All of the materials that form the attachment structure 900, as well as the presence or dumb transponder 910 and the RFID transponder 906 may retain their structural and functional integrity when exposed to elevated temperatures and/or pressures and/or ionizing radiation dosages commonly employed during sterilization of objects to be used in medical applications, such as clinical or surgical procedures, as previously specified herein. One or more components or structures may be protected or shielded, for instance by an encapsulant that retains its structural and functional integrity when exposed to elevated temperatures and/or pressures and/or ionizing radiation dosages commonly employed during sterilization of objects to be used in medical applications, such as clinical or surgical procedures, as previously specified herein.

Figure 10:
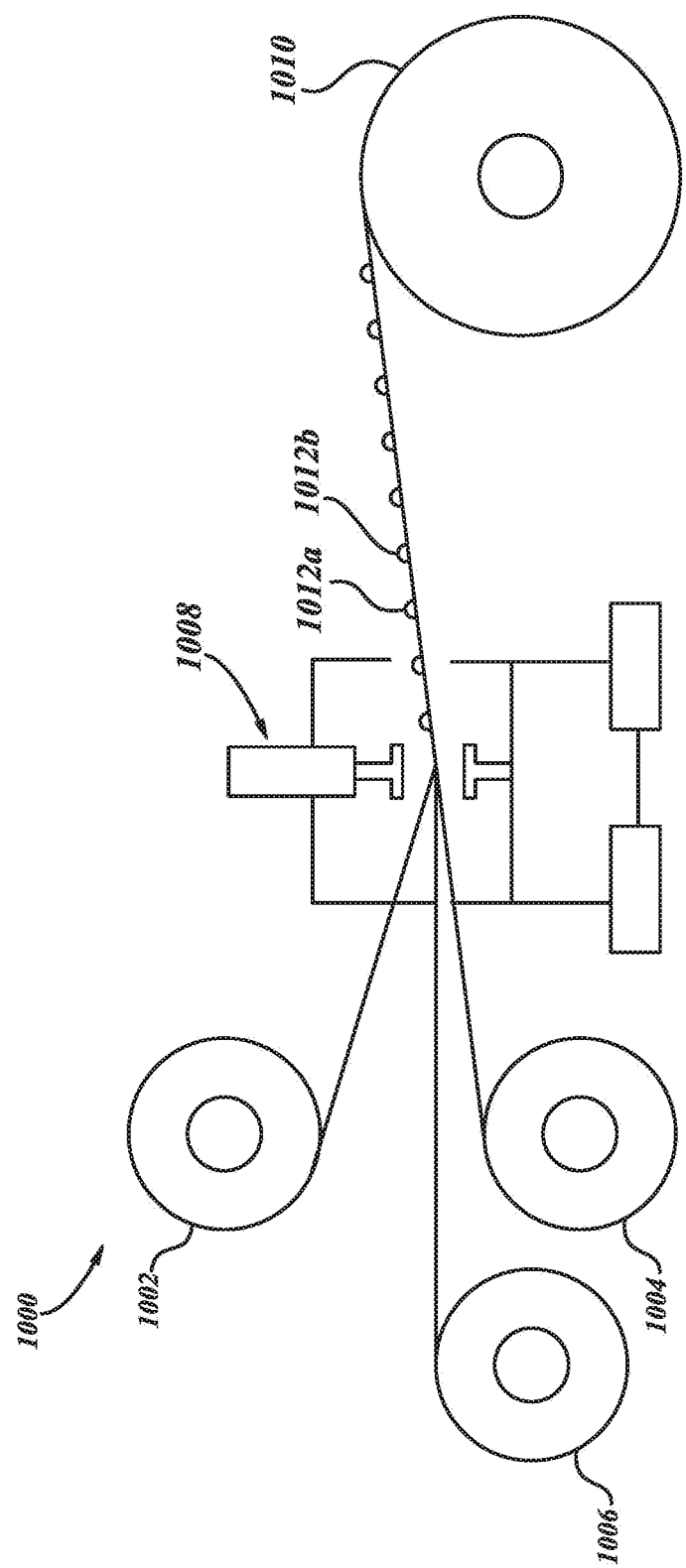
FIG. 10 is a schematic diagram of a manufacturing system to manufacture wirelessly detectable medical objects using continuous web and RF or heat welding techniques, according to one illustrated embodiment, the wirelessly detectable medical objects which maintain structural and functional integrity under sterilization procedures and conditions.

FIG. 10 a manufacturing system 1000 to manufacture wirelessly detectable medical procedure objects using heat or RF welding, according to one illustrated embodiment.

In particular, the system 1000 may provide a web of first flexible layer material 1002 from a spool of first flexible layer material; a web of second flexible layer material 1006 from a spool of second flexible layer material; and a web of adhesive layer material 1004 from a spool of adhesive layer material. For example, either or both of the first flexible layer 1002 and the second flexible layer 1006 may be the same as or similar to layers 208 and 210 discussed with reference to FIG. 2A. The adhesive layer 1004 may be the same as or similar to adhesive layer 212 of FIG. 2A. In some implementations, as shown in FIG. 10, the first and/or second flexible layers 1002 and 1006 and/or adhesive layer material 1004 may be provided as rolls or spools of material, or alternatively as sheets of flexible layers. Alternatively, the adhesive layer material 1004 may be provided as a liquid or gel, and sprayed, printed, painted, deposited or otherwise applied. Further, in some implementations, a roll of absorbent material or gauze to fabricate sponges (not shown in FIG. 10) may also be provided.

The system 1000 may include a welder, welding unit or welding machine 1008 to heat or RF weld the first flexible layer 1002 to the second flexible layer 1006 to form a plurality of pouches (e.g., pouches 1012 a and 1012 b). The adhesive layer 1004 may be physically coupled (e.g., by RF welding or other techniques or via adhesion due to the adhesive property of the adhesive layer 1004) to at least the second flexible layer 1006 opposite the first flexible layer 1002.

Each of the plurality of pouches can be formed by a set of heat or RF welds. For example, welding machine 1008 (e.g., heat or RF welding machine) can be used to create a plurality of heat or RF welds that physically couple the first flexible layer 1002 to the second flexible layer 1006 and create the plurality of pouches 1012 a and 1012 b. Each set of heat or RF welds can take the form of a hollowed rectangle, circle, oval, or other shape to form an interior cavity within a perimeter of the hollowed area. One or more transponders can be sealed within the interior cavity (not illustrated in FIG. 10) of each pouch 1012.

Thus, through autonomous or automatic or manual operation of the RF welding machine 1008 to generate a plurality of heat or RF welds, the first and second flexible layers 1002 and 1006 are transformed into a sheet or roll of pouches 1010, with each pouch 1012 retaining one or more wireless transponders. As such, rather than being discretely made from the assembly of individual components, web based media and continuous web manufacturing techniques may fabricate the pouches 1012 as a continuous web and hence a roll of pouches 1010, each pouch 1012 containing one or more respective wireless transponders. Employing web media based techniques enhances the efficiency in the manufacturing process, as all that remains to be done is cutting or separating the pouches 1012 from the roll 1010 and attaching each of the pouches 1012 to a respective surgical object (e.g., via adhesive layer 1004).

Figure 11:
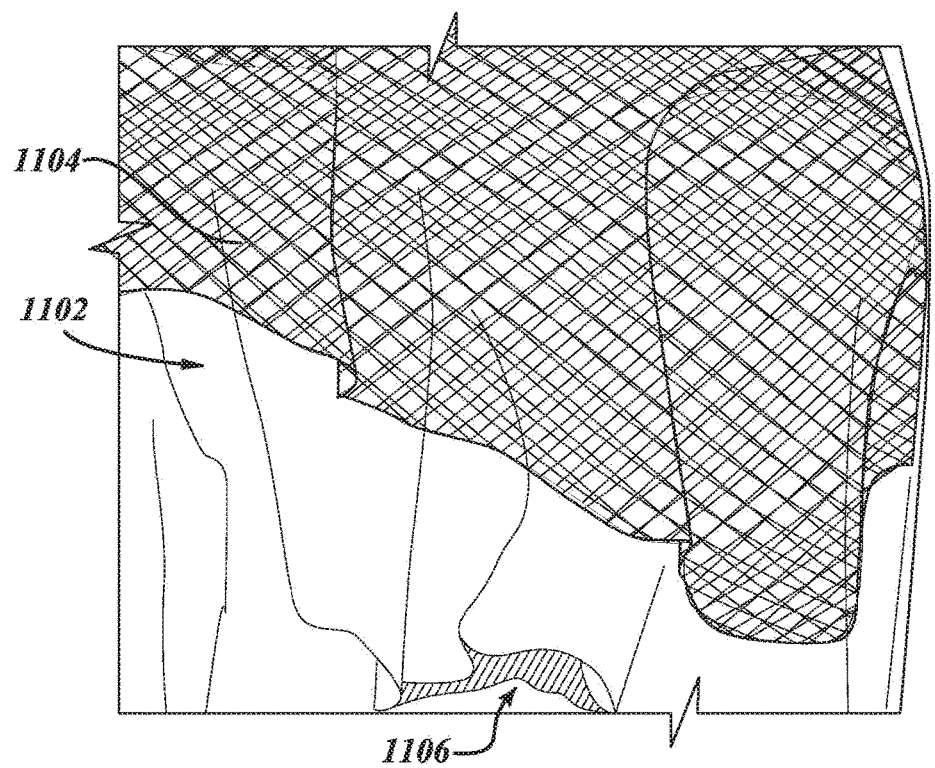
FIG. 11 shows flexible layers usable to manufacture a plurality of pouches, according to one illustrated embodiment, all of which maintain structural and functional integrity under sterilization procedures and conditions.

FIG. 11 shows flexible layers usable to manufacture a plurality of pouches, according to one illustrated embodiment.

In particular, FIG. 11 shows a first flexible layer 1104 of nylon; a second flexible layer 1102 of thermoplastic polyurethane; and an adhesive layer 1106. The above noted materials are provided as examples only. In particular, the flexible layers 1104 and 1102 may be the same as or similar to layers 208 and 210 discussed with reference to FIG. 2A.

All of the materials that form the pouches of FIG. 11, as well as the presence or dumb transponder and the RFID transponder retained or carried thereby, may retain their structural and functional integrity when exposed to elevated temperatures and/or pressures and/or ionizing radiation dosages commonly employed during sterilization of objects to be used in medical applications, such as clinical or surgical procedures, as previously specified herein.

Figure 12:
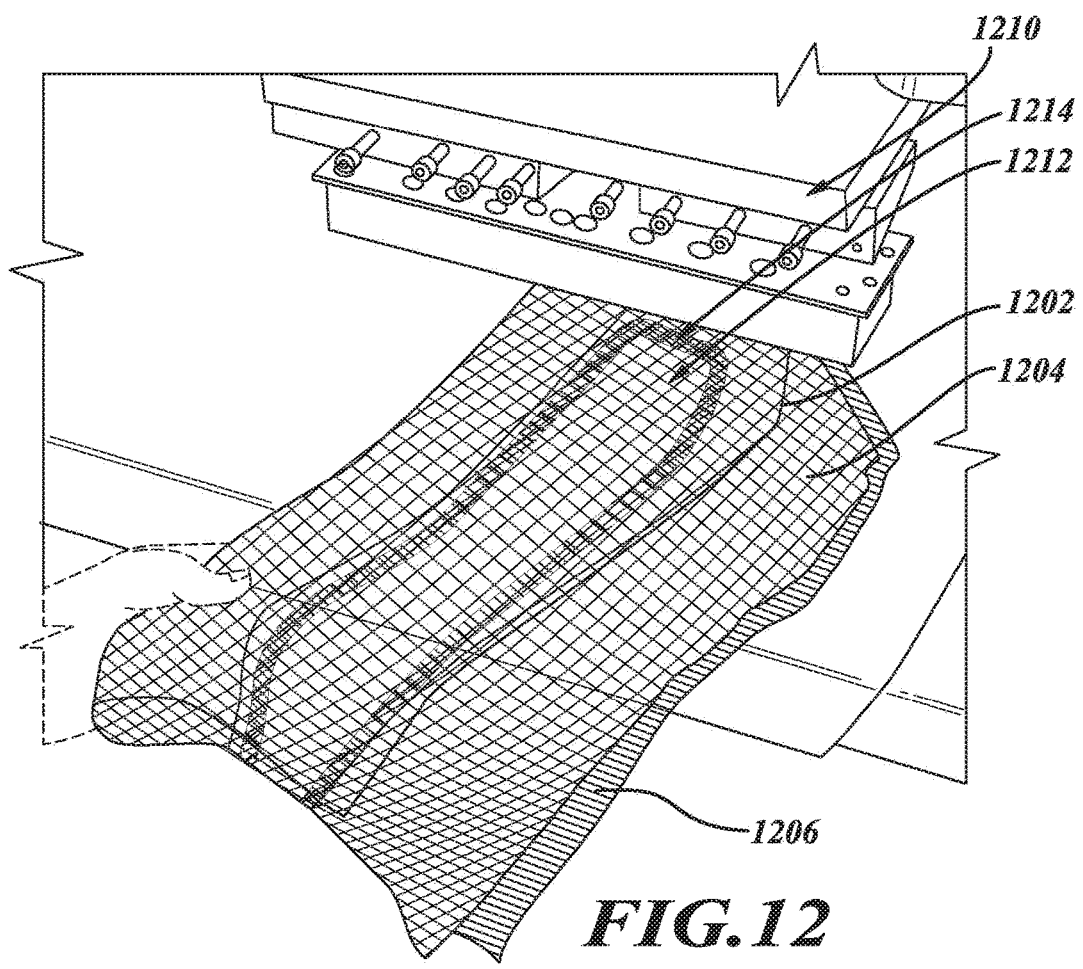
FIG. 12 shows manufacture of a plurality of pouches using an RF or heat welding technique, according to one illustrated embodiment, which maintains structural and functional integrity under sterilization procedures and conditions.

FIG. 12 shows manufacture of a plurality of pouches using an RF or heat welding technique, according to one illustrated embodiment.

In particular, FIG. 12 shows the first flexible layer 1204 of nylon; the second flexible layer 1202 of thermoplastic polyurethane; and the adhesive layer 1206. An RF or heat welding machine 1210 is used to generate a plurality of RF welds to physically couple layer 1102 to layer 1104 and/or adhesive layer 1206 and form a plurality of pouches. As an example, an RF or heat weld 1214 forms at least a portion of a perimeter of an interior cavity of an unfinished pouch 1212. One or more transponders (not shown) may be positioned between layers 1102 and 1104 and then sealed within the pouch 1212 by an additional RF or heat weld.

As one example method of manufacture, the pouches may be made by RF or heat welding the first layer 1204 to the second layer 1202 where a series of cavities for receiving one or more corresponding transponders are made by providing bulges in the first layer 1204 and/or the second layer 1202. The bulges may be formed by bunching or stretching the material of the first layer 1204 and/or the second layer 1202.

Figure 13:
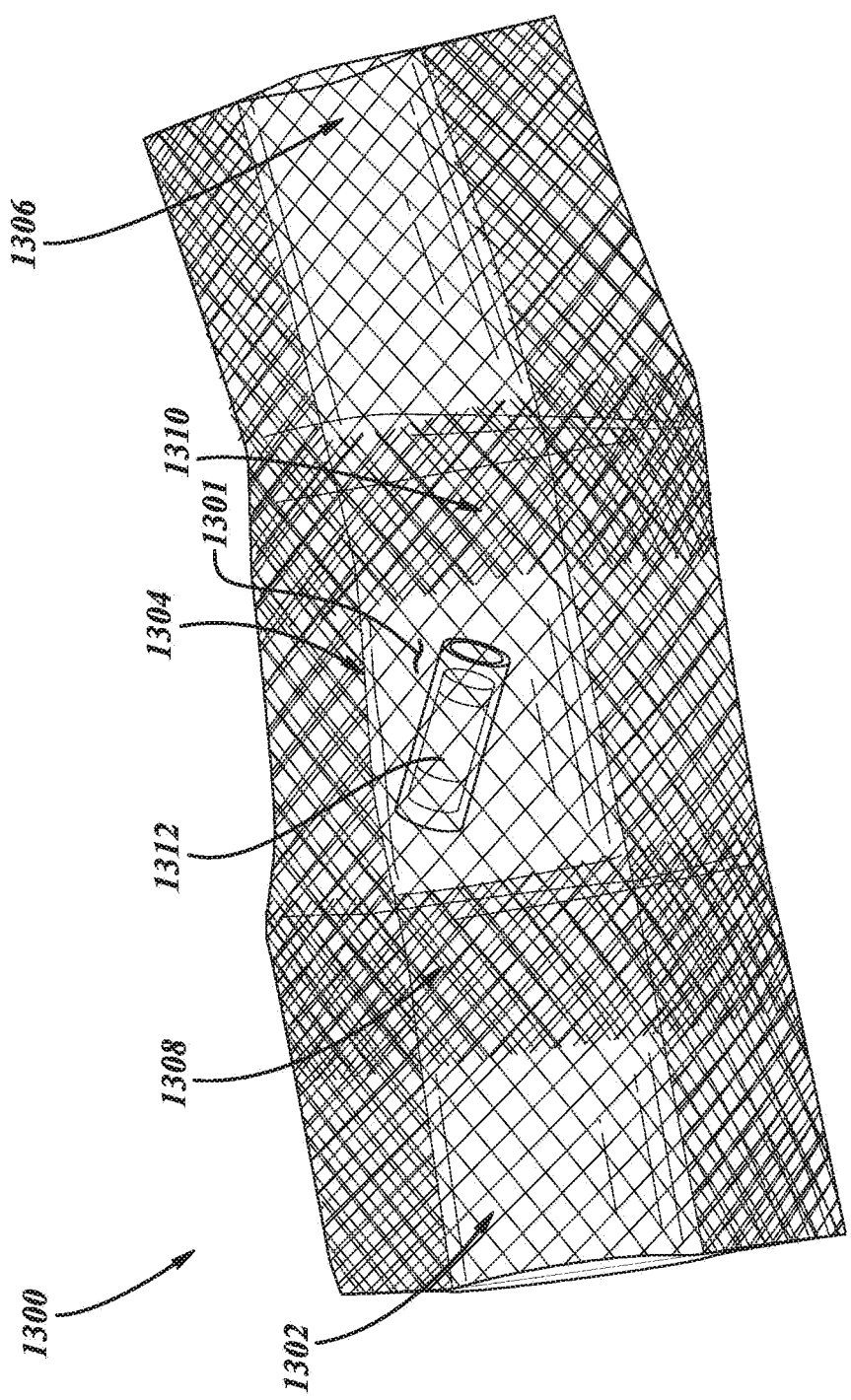
FIG. 13 is a front view of a plurality of pouches manufactured using an RF or heat welding technique, according to one illustrated embodiment, the pouches which maintain structural and functional integrity under sterilization procedures and conditions.

FIG. 13 a web 1300 of a plurality of pouches 1302, 1304, and 1306 manufactured using the RF or heat welding technique illustrated in FIGS. 10 and 12, according to one illustrated embodiment. In particular, a plurality of RF or heat welds form each of pouches 1302, 1304, and 1306. For example, RF or heat welds 1308 and 1310 form at least a portion of a perimeter of an interior cavity of pouch 1304. A presence or dumb transponder 1312 is received and freely movable within the interior cavity 1301 of pouch 1304. Pouches 1302 and 1306 are bisected for the purposes of illustration. The pouches 1302, 1304, and 1306 may be physically separated (e.g., cut apart) and then respectively physically coupled to surgical objects to act as wirelessly detectable objects (e.g., via use of an adhesive layer).

FIGS. 14A-14E sequentially show a piece of gauze 1400 being folded from a pre-folded configuration into a folded configuration as a sponge 1401 (FIGS. 14D, 14E), according to at least one illustrated embodiment. In the particular folded configuration illustrated, the sponge 1401 may advantageously be easier to detect and/or distinguish from neighboring sponges in a set, packet or package of sponges, using imaging techniques, described herein, due to the resulting orientation and/or spacing of radio-opaque material 1422, 1424 and/or wireless transponder 1426 in a pouch 1428.

Figure 14A:
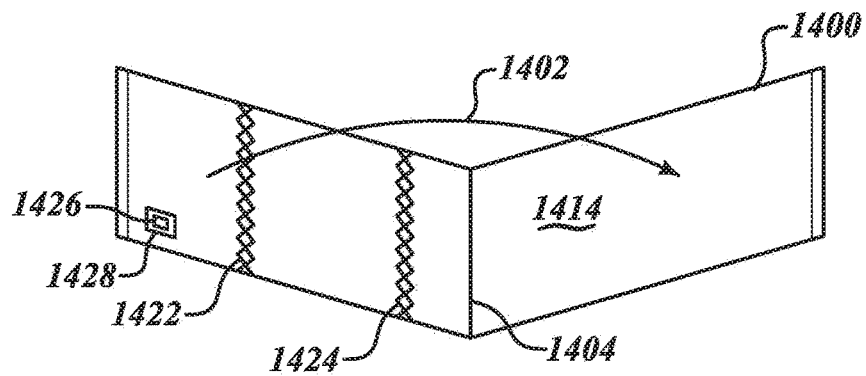
FIG. 14A shows a piece of gauze with first and second radio-opaque material and a wireless transponder, being folded across a first fold-line, according to at least one illustrated embodiment.

FIG. 14A shows a piece of absorbent material or gauze 1400 similar or even identical to those previously described and illustrated, with first and second radio-opaque material 1422, 1424 and a wireless transponder 1426.

All of the materials that form the wireless transponder 1426 (e.g., presence or dumb transponder and the RFID transponder) and/or which retain the wireless transponder 1426 to the piece of absorbent material or gauze 1400, may retain their structural and functional integrity when exposed to elevated temperatures and/or pressures and/or ionizing radiation dosages commonly employed during sterilization of objects to be used in medical applications, such as clinical or surgical procedures, as previously specified herein.

Notably, the first and second radio-opaque material 1422, 1424 are positioned on a same half of the piece of gauze 1400 with respect to a longitudinal middle or center of the piece of gauze 1400 (i.e., middle along the longitudinal axis as the piece of gauze lies flat). As illustrated by arrow 1402 in FIG. 14A, a first portion or panel of the piece of gauze 1400 is folded across a first fold-line 1404 such that two resulting portions of the first major face 1414 are brought together, facing one another. In some implementations, ends of the piece of gauze 1400 opposed to one another along a length of the piece of gauze 1400 may each be folded over itself, and stitched or otherwise secured before the folding of the piece of gauze 1400 into a sponge. This may reduce the chance of stray material or fibers from separating from the piece of gauze 1400.

Figure 14B:
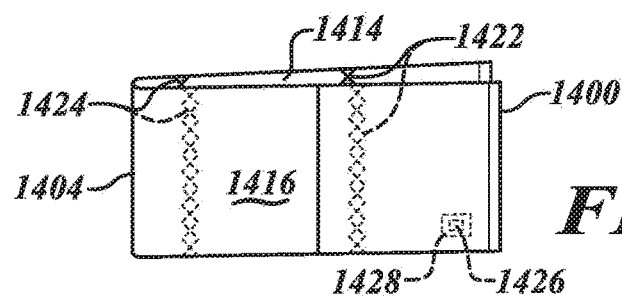
FIG. 14B shows the piece of gauze of FIG. 14A folded across the first fold-line, one half of the piece of gauze overlying the other half of the piece of gauze, according to at least one illustrated embodiment.

FIG. 14B shows the piece of gauze 1400 of FIG. 14A folded across the first fold-line 1404, one half of the piece of gauze 1400 overlying the other half of the piece of gauze 1400. As illustrated in FIG. 14B, the second major face 1416 is on an exterior the partially folded piece of gauze 1400, while the first major face 1414 is now on an interior of the partially folded piece of gauze 1400. Notably, the first and second radio-opaque material 1422, 1424 are positioned on respective halves of the partially folded piece of gauze 1400 with respect to a longitudinal middle or center of the partially folded piece of gauze 1400.

Figure 14C:
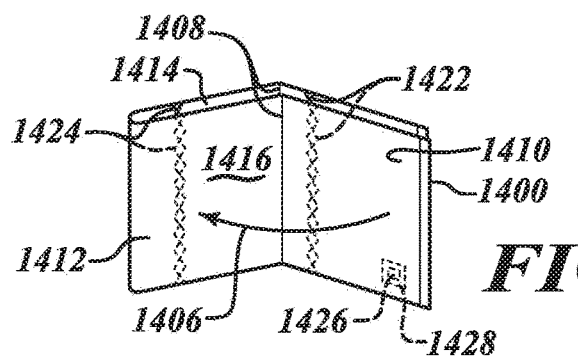
FIG. 14C shows the piece of gauze of FIG. 14B being folded across a second fold-line, according to at least one illustrated embodiment.

As illustrated by arrow 1406 in FIG. 14C, the piece of gauze 1400 is folded across a second fold-line 1408 such that the two halves of the first major face 1414 of the partially folded piece of gauze 1400 are brought together, facing one another.

Figure 14D:
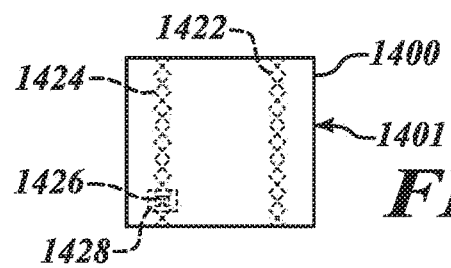
FIG. 14D shows the piece of gauze of FIG. 14C folded across the second fold-line in a folded configuration, four portions of the piece of gauze overlying one another with the radio-opaque material on respective inner pieces or panels of the piece of gauze with respect to a pair of outer pieces or panels of the piece of gauze, according to at least one illustrated embodiment.
Figure 14E:
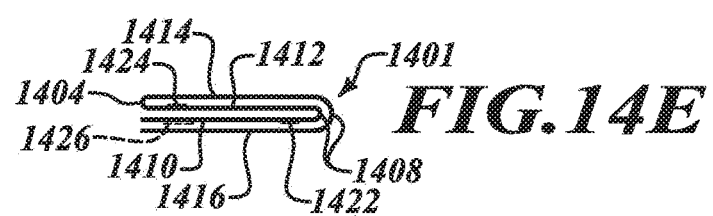
FIG. 14E is top elevational view of the piece of gauze of FIG. 14D in the folded configuration, better illustrating the four portions of the piece of gauze overlying one another with the radio-opaque material on respective inner pieces or panels of the piece of gauze with respect to a pair of outer pieces or panels of the piece of gauze.

FIGS. 14D and 14E show the piece of gauze 1400 of FIG. 14C folded across the second fold-line 1404 in a folded configuration, four portions of the piece of gauze 1400 overlying one another. Notably, the radio-opaque material 1422, 1424 is carried by respective inner pieces or panels 310, 312 of the piece of gauze 1400 or sponge 1401, with respect to a pair of outer pieces or panels 314, 316 of the piece of gauze 1400 or sponge 1401. As best seen in FIG. 14E, the sponge 1401 includes two folds and results in four pieces or panels overlying one another, in a nested configuration, with the radio-opaque material 1422, 1424 spaced relatively inward of the outer most panels or pieces 314, 316 and on distinctly panels or pieces 310, 312 from one another, advantageously enhancing detectability using imaging techniques. Further, the transponder 1426 may overlie one of the radio-opaque material 1422, 1424 when viewed from a resulting major face of the sponge 1401, advantageously enhancing detectability.

For example, the piece of gauze 1400 may be folded once, i.e., into two panels, which may be denominated as a V-fold. The piece of gauze 1400 may be folded twice, i.e., into three panels. There are two possible configurations for three panels, A first configuration is denominated as a Z-fold, which sandwiches a middle panel (i.e., middle along a length of the piece of gauze 1400) between two end panels (i.e., ends along the length of the piece of gauze 1400). A second configuration is denominated as a C-fold, in which one of the end panels (i.e., end along a length of the piece of gauze 1400) is sandwiched between the other end panel and the middle panel (i.e., middle along a length of the piece of gauze 1400).

Figure 15A:
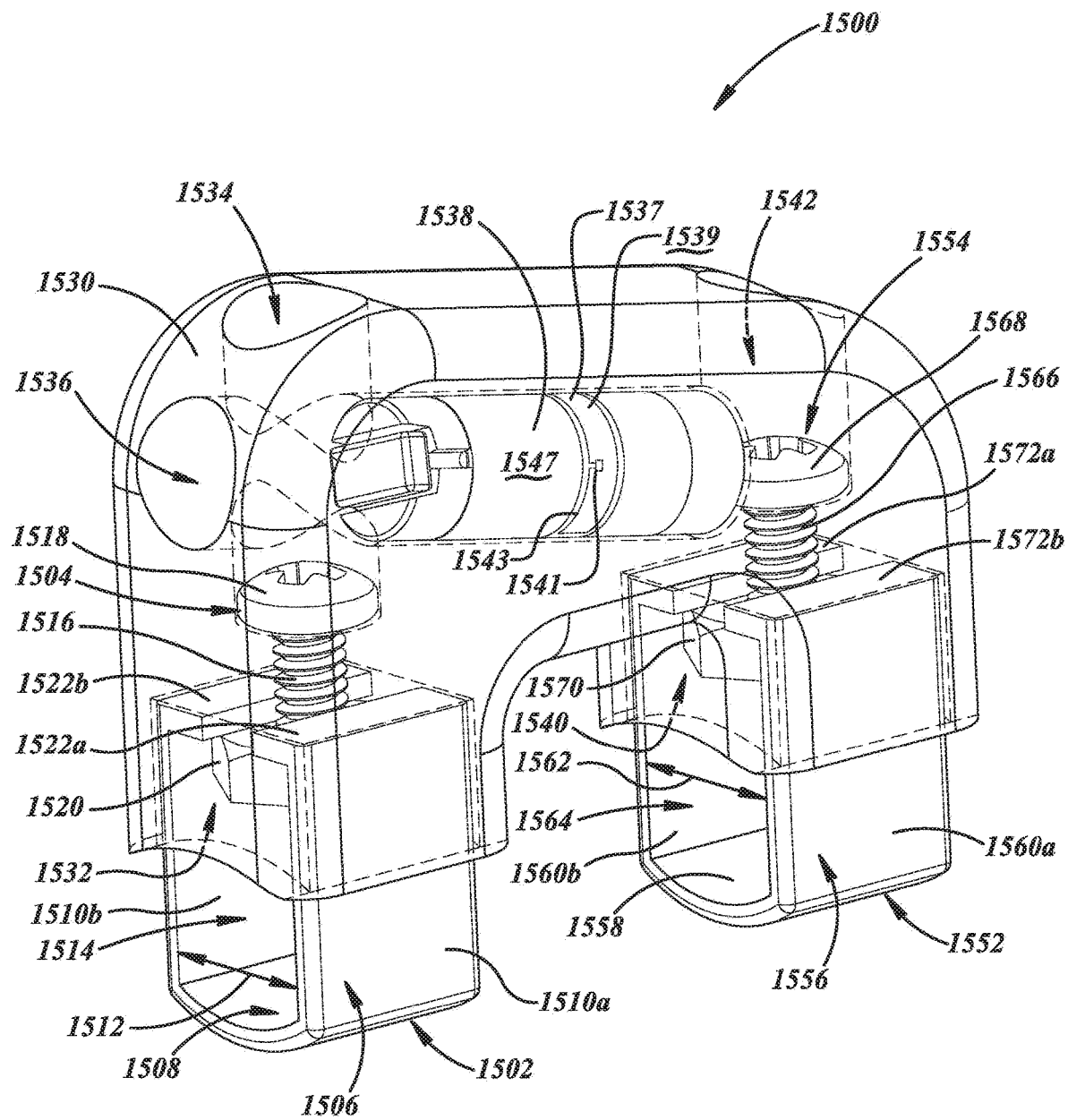
FIG. 15A is a schematic diagram showing a surgical environment illustrating use of an interrogation and detection system to detect one or more objects tagged with a transponder in a patient, according to at least one illustrated embodiment.
Figure 15B:
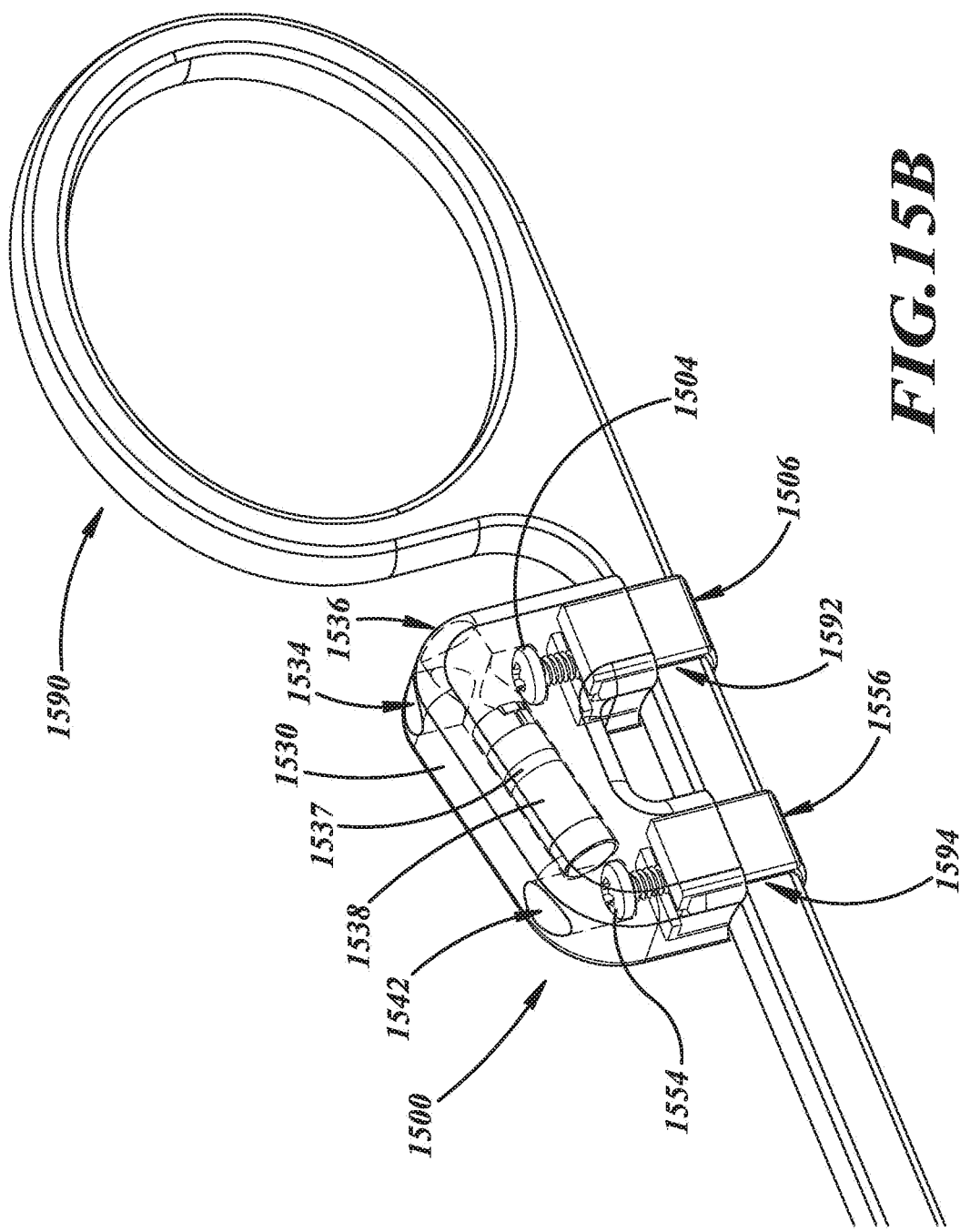
FIG. 15B is an isometric view of an apparatus to physically couple one or more transponders to a surgical object, according to at least one illustrated embodiment.

FIGS. 15A and 15B show an apparatus 1500 to physically couple at least one wireless transponder (e.g., RFID transponder 1537, presence or dumb transponder 1538) to a medical procedure object, for instance an instrument 1590. In particular, FIG. 15A shows the apparatus 1500 not physically coupled to the medical procedure object 1590 while FIG. 15B shows the apparatus 1500 physically coupled to the medical procedure object 1590.

As illustrated, the apparatus 1500 may physically couple both an RFID transponder 1537 and a presence or dumb transponder 1538 to a medical procedure object, for instance instrument 1590. The RFID transponder 1537 may be formed as a flexible tag, employing a flexible substrate 1539 (e.g. relatively few layers of FR4) which carries an RFID integrated circuit 1541 and antenna 1543 (e.g. electrically conductive trace) communicatively coupled to the RFID integrated circuit 1541. The RFID transponder 1537 may be physically coupled to the presence or dumb transponder 1538. For example, the RFID transponder 1537 may at least partially wrap about an exterior periphery or exterior surface 1547 of the presence or dumb transponder 1538. The RFID transponder 1537 may be attached to the presence or dumb transponder 1538 via an adhesive or may be retained thereto under pressure.

All of the materials that form the wireless transponders (e.g., RFID transponder 1537, presence or dumb transponder 1538) and/or which attaches the RFID transponder 1537 to the presence or dumb transponder 1538, may retain their structural and functional integrity when exposed to elevated temperatures and/or pressures and/or ionizing radiation dosages commonly employed during sterilization of objects to be used in medical applications, such as clinical or surgical procedures, as previously specified herein.

The apparatus 1500 includes a first clamp 1502, a second clamp 1552, and a housing 1530. The housing 1530 is transparently depicted for the purposes of illustrating certain features of the apparatus 1500 internal to the housing 1530. However, the housing 1530 is typically not transparent.

The first clamp 1502 includes a first fastener 1504 and a first channel member 1506. The first channel member 1506 has a first base 1508 and a first pair of side portions 1510 *a* and 1510 *b* that extend from the first base 1508. The first pair of side portions 1510 *a* and 1510 *b* are opposed to one another across a width 1512 of the first channel member 1506 to form a first channel 1514 therebetween. The width 1512 of the first channel 1514 is sized to receive at least a first portion 1592 of the medical procedure object 1590 therein.

The first channel member 1506 may be metal, plastic, and/or other materials. The first channel member 1506 may be a single integral piece or may be formed from multiple components. For example, one or more bending operations may shape a single band of metal into the first channel member 1506. Alternatively, the first pair of side portions 1510 *a* and 1510 *b* may be separate pieces that are physically coupled to the first base 1508 (e.g., by welding).

As shown best in FIG. 15A, the first base 1508 is curved to accommodate a curved surface of the medical procedure object 1590 (e.g., a curved surface of an elongated handle portion or elongated member of the medical procedure object 1590). In some implementations, the first side portions 1510 *a* and 1510 *b* are similarly curved to accommodate a portion of the medical procedure object 1590 with multiple curved surfaces (e.g., a cylindrical portion). However, in some implementations, neither the first base 1508 nor the first side portions 1510 *a* and 1510 *b* are curved, thereby accommodating a portion of the medical procedure object 1590 with a rectangular cross-section.

Similar to first clamp 1502, the second clamp 1552 includes a second fastener 1554 and a second channel member 1556. The second channel member 1556 has a second base 1558 and a second pair of side portions 1560 *a* and 1560 *b* that extend from the second base 158. The second pair of side portions 1560 *a* and 1560 *b* are opposed to one another across a width 1562 of the second channel member 1556 to form a second channel 1564 therebetween. The width 1562 of the second channel 1564 is sized to receive at least a second portion 1594 of the medical procedure object 1590 therein. The second channel member 1556 may be constructed as discussed above with respect to the first channel member 1506.

The housing 1530 has a first cavity 1532, a second cavity 1540, a first passageway 1534, a second passageway 1536, and a third passageway 1542. The first cavity 1532 receives at least a portion of the first pair of side portions 1510 *a* and 1510 *b* of the first channel member 1506. The second cavity 1540 receives at least a portion of the second pair of side portions 1560 *a* and 1560 *b* of the second channel member 1556.

The housing 1530 may be non-metallic (e.g., formed of one or more plastics) to prevent the housing 1530 from impeding or interfering with accurate detection of the transponder 1538 by the detection and interrogation system 5. In some implementations, the housing 1530 is a single, integral piece of plastic formed through a molding process. For example, the passageways 1534, 1536, and 1542 may be defined within the housing 1530 during the molding process. Alternatively, one or more drilling operations may create the passageways 134, 1536, and 1542 in the single, integral piece of plastic. In other implementations, the housing 130 comprises two or more portions that are secured together after manufacturing. For example, the housing 1530 may consist of two body portions that snap together or otherwise have means for coupling to each other (e.g., a complementary peg and hole, clasps, etc.). The housing 1530 may be rigid and non-elastic or may exhibit some elasticity.

The housing 1530 may retain its structural and functional integrity when exposed to elevated temperatures and/or pressures and/or ionizing radiation dosages commonly employed during sterilization of objects to be used in medical applications, such as clinical or surgical procedures, as previously specified herein.

As shown best in FIG. 15A, the first passageway 1534 extends in a first direction, the second passageway 1536 extends in a second direction, and the third passageway 1542 extends in a third direction. The third direction is parallel to the first direction and the second direction is not parallel to the first and the third directions. In some implementations, the second direction is substantially perpendicular to the first and third directions.

The first passageway 1534 receives the first fastener 1504. The first passageway 1534 opens at least in part into the first cavity 1532 to permit the first fastener 1504 to extend at least in part into the first cavity 1532 and adjustably engage with the first channel member 1506. In particular, the first fastener 1504 includes a first screw that has a head 1518 and an elongated shaft 1516. The shaft 1516 has a first diameter and the head 1518 has a second diameter that is greater than the first diameter. The first passageway 1534 includes an outer portion that has a third diameter that is greater than the second diameter and an inner portion that has a fourth diameter that is greater than the first diameter and less than the second diameter. As such, the first passageway 1534 defines a first shelf at a first transition between the outer portion and the inner portion of the first passageway 1534. The head 1518 of the first screw engages the first shelf.

The first fastener 1504 adjustably engages with the first channel member 1506 to securingly clamp the first portion 1592 of the medical procedure object 190 in the first channel 114 of the first channel member 1506. More particularly, the shaft 1516 has external threading. The first fastener 1504 further includes a first nut 1520 that securingly receives the shaft 1516 (e.g., has internal threading complementary to the external threading of the shaft 1516). The first channel member 106 further includes a first pair of flanges 1522 *a* and 1522 *b* that respectively extend from the first pair of side portions 1510 *a* and 1510 *b* into the first channel 1514. The first nut 1520 is positioned between the first pair of flanges 1522 *a* and 1522 *b* and the first base 1508. The first nut 1520 physically engages the first pair of flanges 1522 *a* and 1522 *b*.

Alternatively, a twist tie may be used, for example as a wire or metal suture where the twist tie replaces the channel member and the fastener. In particular, a wire or metal suture may form a loop through which a portion of the instrument 1590 is received, and the end portions of the wire or metal suture are twisted together to secure the housing 1530 to the instrument 1590. Such is illustrated in U.S. provisional patent application Ser. No. 62/138,248 (now U.S. Patent Publication Nos. 2016/0210548; 2018/0000556; and 2018/0333309).

Thus, for example, the shaft 1516 extends from the first passageway 1534 into the first cavity 1532 to securingly and adjustably engage with the first nut 1520. The first nut 1520 physically engages the first pair of flanges 1522 *a* and 1522 *b*. Rotation of the first screw in a first rotational direction will therefore result in the first clamp 1502 being tightened to securingly clamp the first portion 192 of the medical procedure object 190 in the first channel 1514. Likewise, rotation of the first screw in a second rotational direction opposite the first will result in the first clamp 1502 being loosened.

The third passageway 1542 receives the second fastener 1554 and opens at least in part into the second cavity 1540 to permit the second fastener 1554 to extend at least in part into the second cavity 1540 and adjustably engage with the second channel member 1556. In particular, the second fastener 1554 includes a second screw that has a head 1568 and an elongated shaft 1566. The shaft 166 has the first diameter and the head 1568 has the second diameter that is greater than the second diameter. The second passageway 1542 includes an outer portion that has the third diameter that is greater than the second diameter and an inner portion that has the fourth diameter that is greater than the first diameter and less than the second diameter. As such, the second passageway 1542 defines a second shelf at a second transition between the outer portion and the inner portion of the second passageway 1542. The head 1568 of the second screw engages the second shelf.

The second fastener 1554 adjustably engages with the second channel member 1556 to securingly clamp the second portion 1594 of the medical procedure object 1590 in the second channel 1564 of the second channel member 1556. More particularly, the shaft 166 has external threading and the second fastener 1554 further includes a second nut 1570 that securingly receives the shaft 1566 (e.g., has internal threading complementary to the external threading of the shaft 1566). The second channel member 1556 further includes a second pair of flanges 1572 a and 1572 b that respectively extend from the second pair of side portions 1560 a and 1560 b into the second channel 1564. The second nut 170 is positioned between the second pair of flanges 1572 a and 1572 b and the second base 1558. The second nut 1570 physically engages the second pair of flanges 1572 a and 1572 b.

Thus, for example, the shaft 1566 extends from the second passageway 1542 into the second cavity 1540 to securingly and adjustably engage with the second nut 1570. The second nut 1570 physically engages the second pair of flanges 1572 a and 1572 b. Rotation of the second screw in a first rotational direction will therefore result in the second clamp 1552 being tightened to securingly clamp the second portion 194 of the medical procedure object 1590 in the second channel 1564. Likewise, rotation of the second screw in a second rotational direction opposite the first will result in the second clamp 1552 being loosened.

The second passageway 1536 receives at least one wireless transponder 1537, 1538 that wirelessly receives and returns signals. The wireless transponder 1537, 1538 may be constructed in various manners. For example, an LC resonant or dumb transponder 1538 may include a ferrite rod with a conductive coil wrapped about an exterior surface thereof to form an inductor, and a capacitor coupled to the conductive coil to form a series circuit. The conductive coil may, for example, take the form of a spiral wound conductive wire with an electrically insulative sheath or sleeve. In other implementations, an RFID transponder 1537 includes an RFID chip 1541 that stores identification information that uniquely identifies the transponder 1537. Additional details about types of transponders may be found in U.S. Provisional Patent Application No. 60/811,376 filed Jun. 6, 2006 (U.S. Patent Publication No. 2007/0285249); U.S. Provisional Patent Application No. 60/892,208 filed Feb. 28, 2007 (U.S. Pat. No. 8,710,957); and U.S. Provisional Patent Application No. 62/106,052 filed Jan. 21, 2015 (now U.S. Patent Publication Nos. 2016/0206399; 2016/0210548; 2018/0000556; and 2018/0333309), each of which are herein incorporated by reference.

The second passageway 1536 intersects the first passageway 1534. In particular, the second passageway 1536 intersects the outer portion of the first passageway 1534. The second passageway 136 has a fifth diameter at least greater than the second diameter of the head 1518 of the first fastener 1504.

In some implementations, an encapsulant (not shown) fills the portions of each of passageways 1534, 1536, and 1542 that are respectively unoccupied by the first fastener 1504, the transponder 1538, and the second fastener 1554. The encapsulant may be shaped to substantially match an exterior surface of the housing 1530 and thereby contribute to a substantially continuous exterior surface of the apparatus 1500. The encapsulant may ensure that the first fastener 1504, the transponder 1538, and the second fastener 1554 are physically secured in their respective positions and/or prevent contaminants from entering the passageways 1534, 1536, and 1542.

In some implementations, the encapsulant is capable of withstanding multiple rounds of sterilization of the apparatus 100 by one or more of autoclaving, electron beam or isotope radiation, ethylene oxide, plasma or corona discharge, and liquid sterilants. In some implementations, the encapsulant is a biocompatible epoxy. In some implementations, the encapsulant may be readily removed from at least passageways 1534 and 1542 to permit removal of the apparatus 1500 from the instrument 1590. For example, the encapsulant may be removed via drilling or mechanical abrasion.

The housing 1530 is preferably transparent to electromagnetic energy at least in the wavelengths at which the wireless transponders 1537, 1538 operate.

Furthermore, in some implementations, the apparatus 1500 is manufactured and distributed without a transponder 1538 attached or received within the housing 1530. Advantageously, a transponder 1538 compatible with a particular detection and interrogation system can be placed into the apparatus 1500 at a subsequent time, for example by the end-user.

The above description of illustrated embodiments, including what is described in the Abstract, is not intended to be exhaustive or to limit the various embodiments to the precise forms disclosed. Although specific embodiments of and examples are described herein for illustrative purposes, various equivalent modifications can be made without departing from the spirit and scope of the disclosure, as will be recognized by those skilled in the relevant art.

The teachings provided herein can be applied to other absorbent materials, other types of transponders, and other interrogation and detection systems. For instance, the transponder device may be used to mark objects anytime detection of the presence of marked objects is desirable in a confined area, not just during surgery. For example, it may be used to make sure marked objects are not left inside a machine (e.g., vehicle, copy machine) after maintenance is performed. In at least some embodiments, the transponder housing may be utilized to mark objects to determine the removal of a marked object from a confined area, such as a cover-all garment from a clean room of a semiconductor fabrication plant. In such an embodiment, an interrogation device, for example, may be placed proximate to a door of the confined area.

In addition, a transponder pouch may be manufactured and distributed for tagging objects without a transponder currently attached or received therein. Advantageously, the pouch can then be used to place a transponder compatible with a particular detection and interrogation system at a subsequent time, including by the end-user.

The various embodiments described above can be combined to provide further embodiments. To the extent that they are not inconsistent with the specific teachings and definitions herein, all of the commonly assigned U.S. patents, U.S. patent application publications, U.S. patent applications referred to in this specification, including but not limited to U.S. Pat. Nos. 8,358,212; 8,710,957; 8,726,911; U.S. Patent Application Publication No. 2010/0108079; U.S. Provisional Patent Application Ser. No. 60/811,376 filed Jun. 6, 2006 (now U.S. Patent Publication No. 2007/

0285249); U.S. Provisional Patent Application Ser. No. 60/892,208, filed Feb. 28, 2007 (now U.S. Pat. No. 8,710, 957); U.S. Provisional Patent Application Ser. No. 61/109, 142 filed Oct. 28, 2008 (now U.S. Patent Publication Nos. 2010/0108079; 2014/0303580 and 2018/0000555); U.S. Provisional Patent Application Ser. No. 62/106,052 filed Jan. 21, 2015 (now U.S. Patent Publication Nos. 2016/ 0206399; 2016/0210548; 2018/0000556; and 2018/ 0333309); U.S. Provisional Patent Application Ser. No. 62/121,358 filed Feb. 26, 2015 (now U.S. Patent Publication Nos. 2016/0250000 and 2019/0223980); U.S. Provisional Patent Application Ser. No. 62/138,248 filed Mar. 25, 2015 (now U.S. Patent Publication Nos. 2016/0210548; 2018/ 0000556; and 2018/0333309); U.S. Provisional Patent Application Ser. No. 62/143,726 filed Apr. 6, 2015 (now U.S. Pat. No. 10,193,209); U.S. Provisional Patent Application Ser. No. 62/164,412 filed May 20, 2015; and U.S. Provisional Patent Application Ser. No. 62/182,294 filed Jun. 19, 2015 are each incorporated herein by reference, in their entirety. Aspects of the embodiments can be modified, if necessary, to employ systems, circuits and concepts of the various patents, applications and publications to provide yet further embodiments.

These and other changes can be made in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure.

What is claimed is:

1. A wirelessly detectable object for use in a medical procedure, comprising:
    a medical procedure object; and
    an attachment structure detachably coupled to the medical procedure object, the attachment structure including:
        a pouch;
        a first transponder; and
        a second transponder,
    wherein the first transponder is freely movable within in the pouch and the second transponder is fixedly secured in the pouch, and
    wherein one of the first or second transponders includes a directional antenna disposed within the pouch.

2. The wirelessly detectable object of claim 1, wherein one of the first or second transponders is configured to receive a first response signal and transmit a first signal, the first signal including non-identification information.

3. The wirelessly detectable object of claim 2, wherein one of the first or second transponders is configured to receive a second response signal and transmit a second signal, the second signal including unique identification information of the medical procedure object.

4. The wirelessly detectable object of claim 1, wherein the pouch includes a first layer and a second layer, wherein the second layer is coupled to the first layer.

5. The wirelessly detectable object of claim 4, wherein one of the first layer or the second layers is a substrate.

6. The wirelessly detectable object of claim 1, wherein the pouch further includes an adhesive layer coupled to the second layer and configured to facilitate coupling of the attachment structure to the medical procedure object.

7. The wirelessly detectable object of claim 1, wherein one of the first or second transponders is disposed in an encapsulant configured to provide shielding from radiation.

8. The wirelessly detectable object of claim 1, wherein the directional antenna includes an active antenna, at least one passive antenna, and an integrated circuit configured to energize the active antenna.

9. The adapter assembly according to claim 1, wherein the medical procedure object is gauze or sponge.

10. An identification and detection system, comprising:
    at least one antenna;
    a controller configured to:
        emit at least one interrogation signal; and
        receive at least one response signal;
    a medical procedure object for use in performing a medical procedure; and
    an attachment structure detachably coupled to the medical procedure object, the attachment structure including:
        a pouch;
        a first transponder; and
        a second transponder,
    wherein the first transponder is freely movable within in the pouch and the second transponder is fixedly secured in the pouch, and
    wherein one of the first or second transponders includes a directional antenna disposed within the pouch.

11. The identification and detection system of claim 10, wherein one of the first or second transponders is configured to receive at least one emitted interrogation signal and transmit to the controller the at least one response signal.

12. The identification and detection system of claim 11, wherein the at least one response signal is one of unique identification information or non-identification information.

13. The identification and detection system of claim 10, wherein the pouch includes a first layer and a second layer, wherein the second layer is coupled to the first layer.

14. The identification and detection system of claim 13, wherein one of the first layer or the second layer is a substrate.

15. The identification and detection system of claim 13, wherein the pouch further includes an adhesive layer coupled to the second layer and configured to facilitate coupling of the attachment structure to the medical procedure object.

16. The identification and detection system of claim 10, wherein one of the first or second transponders is disposed in an encapsulant configured to provide shielding from radiation.

17. The identification and detection system of claim 10, wherein the directional antenna includes an active antenna, at least one passive antenna, and an integrated circuit configured to energize the active antenna.

* * * * *